(12) United States Patent
Mang et al.

(10) Patent No.: US 8,343,972 B2
(45) Date of Patent: Jan. 1, 2013

(54) ORGANIC COMPOUNDS

(75) Inventors: Rosemarie Mang, Vienna (AT); Heinz Berner, Vienna (AT)

(73) Assignee: Nabriva Therapeutics AG, Vienna (AT)

( * ) Notice: Subject to any disclaimer, the term of this patent is extended or adjusted under 35 U.S.C. 154(b) by 0 days.

(21) Appl. No.: 11/997,637

(22) PCT Filed: Jul. 26, 2006

(86) PCT No.: PCT/AT2006/000318
§ 371 (c)(1),
(2), (4) Date: May 12, 2008

(87) PCT Pub. No.: WO2007/014409
PCT Pub. Date: Feb. 8, 2007

(65) Prior Publication Data
US 2008/0306072 A1 Dec. 11, 2008

(30) Foreign Application Priority Data
Aug. 3, 2005 (GB) .................................. 0515995.9

(51) Int. Cl.
*A61K 31/5375* (2006.01)
*A61K 31/215* (2006.01)
*A61P 31/00* (2006.01)
*A61P 31/04* (2006.01)
*C07C 323/13* (2006.01)
*C07D 265/30* (2006.01)

(52) U.S. Cl. .................... 514/239.5; 514/529; 514/530; 544/154; 560/125; 560/121

(58) Field of Classification Search .................. 514/530; 530/121, 125
See application file for complete search history.

(56) References Cited

U.S. PATENT DOCUMENTS
6,753,445 B2 * 6/2004 Ascher et al. ................. 560/125

FOREIGN PATENT DOCUMENTS
WO 02/04414 1/2002
WO 03/082260 10/2003
WO WO 03090740 A1 * 11/2003

OTHER PUBLICATIONS

Vippagunta et al., Advanced Drug Delivery Reviews, vol. 48, p. 3-26 (p. 3), 2001.*

* cited by examiner

*Primary Examiner* — Yong Chu
(74) *Attorney, Agent, or Firm* — Workman Nydegger

(57) ABSTRACT

The present invention relates to compounds selected from the group consisting of 14-O-[((Mono- or dialkylamino)-cycloalkylsulfanyl- or -cycloalkyl-oxy)-acetyl, -thioacetyl or -imino-oxy]-mutilins, 14-O-[((Cycloalkyl- or heterocyclylamino)-cycloalkylsulfanyl- or -cycloalkyl-oxy)-acetyl, -thioaceyl or -imino-oxy]-mutilins, 14-O-[((Heterocyc-N-yl-cycloalkyl)-sulfanyl- or -oxy)-acetyl, -thioacetyl or -imino-oxy]-mutilins, 14-O-[(((Mono- or dialkylamino)-cycloalkyl)-alkylsulfanyl- or -alkyl-oxy)-acetyl, -thioacetyl or -imino-oxy]-mutilins, 14-O-[(((Cycloalkyl- or heterocyclylamino)-cycloalkyl)-alkylsulfanyl- or -alkyl-oxy)-acetyl, -thioacetyl or -imino-oxy]-mutilins, and 14-O-[((Heterocyc-N-yl-cycloalkyl)-alkylsulfanyl- or -alkyl-oxy)-acetyl, -thioacetyl or -imino-oxy]-mutilins, and their use as pharmaceuticals.

18 Claims, No Drawings

ORGANIC COMPOUNDS

The present invention relates to organic compounds, such as pleuromutilins.

Pleuromutilin, a compound of formula A

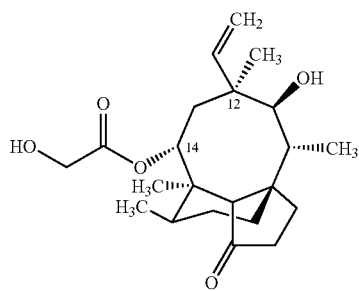

is a naturally occurring antibiotic, e.g. produced by the basidomycetes *Pleurotus mutilus* and *P. passeckerianus*, see e.g. The Merck Index, 13th edition, item 7617.

A number of further pleuromutilins having the principle ring structure of pleuromutilin and being substituted at the hydroxy group have been developed, e.g. as antimicrobials.

We have now found pleuromutilins with interesting activity.

A pleuromutilin provided by the present invention includes a pleuromutilin having the basic structural elements of the mutilin ring system as set out in formula PLEU

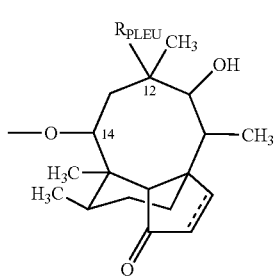

wherein $R_{PLEU'}$ is vinyl or ethyl and the dotted line is a bond or is no bond.

The following numbering system is used in the present application:

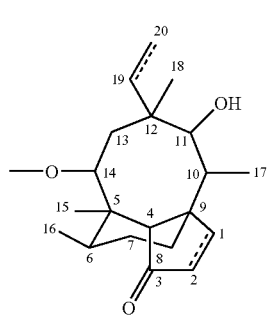

The dotted line between positions 19 an 20 (and between positions 1 and 2) is a bond or is no bond. In a compound of formula A or of formula PLEU a hydrogen atom in positions 4, 7 and/or 8 of the ring system may be replaced by deuterium, and if the dotted line between positions 1 and 2 is no bond (single bond between positions 1 and 2) the ring system may be further substituted in positions 1 and/or 2, e.g. by halogen, deuterium or hydroxy. The group —O— in position 14 is further substituted, preferably by a substituted carbonyl group.

In one aspect the present invention provides a compound, i.e. a pleuromutilin, selected from the group consisting of
14-O-[((Mono- or dialkylamino)-cycloalkylsulfanyl- or -cycloalkyl-oxy)-acetyl, -thioacetyl or -imino-oxy]-mutilins,
14-O-[((Cycloalkyl- or heterocyclylamino)-cycloalkylsulfanyl- or -cycloalkyl-oxy)-acetyl, -thioacetyl or -imino-oxy]-mutilins,
14-O-[((Heterocyc-N-yl-cycloalkyl)-sulfanyl- or -oxy)-acetyl, -thioacetyl or -imino-oxy]-mutilins,
14-O-[(((Mono- or dialkylamino)-cycloalkyl)-alkylsulfanyl- or -alkyl-oxy)-acetyl, -thioacetyl or -imino-oxy]-mutilins,
14-O-[(((Cycloalkyl- or heterocyclylamino)-cycloalkyl)-alkylsulfanyl- or -alkyl-oxy)-acetyl, -thioacetyl or -imino-oxy]-mutilins, and
14-O-[((Heterocyc-N-yl-cycloalkyl)-alkylsulfanyl- or -alkyl-oxy)-acetyl, -thioacetyl or -imino-oxy]-mutilins, preferably,
14-O-[((Mono- or dialkylamino)-cycloalkylsulfanyl- or -cycloalkyl-oxy)-acetyl]-mutilins,
14-O-[((Cycloalkyl- or heterocyclylamino)-cycloalkylsulfanyl- or -cycloalkyl-oxy)-acetyl]-mutilins,
14-O-[((Heterocyc-N-yl-cycloalkyl)-sulfanyl- or -oxy)-acetyl]-mutilins,
14-O-[(((Mono- or dialkylamino)-cycloalkyl)-alkylsulfanyl- or -alkyl-oxy)-acetyl]-mutilins,
14-O-[(((Cycloalkyl- or heterocyclylamino)-cycloalkyl)-alkylsulfanyl- or -alkyl-oxy)-acetyl]-mutilins, and
14-O-[((Heterocyc-N-yl-cycloalkyl)-alkylsulfanyl- or -alkyl-oxy)-acetyl]-mutilins, more preferably
14-O-[((Mono- or dialkylamino)-cycloalkylsulfanyl- or -cycloalkyl-oxy)-acetyl]-mutilins,
14-O-[((Cycloalkyl- or heterocyclylamino)-cycloalkylsulfanyl- or -cycloalkyl-oxy)-acetyl]-mutilins, and
14-O-[((Heterocyc-N-yl-cycloalkyl)-sulfanyl- or -oxy)-acetyl]-mutilins.

According to a preferred embodiment of the invention, the compound is a
14-O-[((Mono- or dialkylamino)-cycloalkylsulfanyl)-acetyl]-mutilin,
14-O-[((Cycloalkyl- or heterocyclylamino)-cycloalkylsulfanyl)-acetyl]-mutilin, or
14-O-[((Heterocyc-N-yl-cycloalkyl)-sulfanyl)-acetyl]-mutilin.

In the above compounds
cycloalkyl is $(C_{3-12})$cycloalkyl, such as $(C_{4-8})$cycloalkyl, e.g. $(C_{5-7})$cycloalkyl,
heterocyclyl includes a heterocyclic group comprising 3 to 7 ring members, preferably 5 to 6 ring members, and one to four, preferably 2, heteroatoms selected from N, O and S, preferably N, O, which heterocyclyl may be anellated with another ring/system, such as $(C_{6-12})$aryl, e.g. phenyl,
"Heterocyc-N-yl-cycloalkyl" means heterocyclyl comprising 5 to 7 ring members and 1 to 4 heteroatoms selected from N, O and S which comprises at least one nitrogen heteroatom, which nitrogen atom is bond to the cycloalkyl, such as morpholin-1-yl,
alkyl is preferably $(C_{1-8})$alkyl, such as $(C_{1-4})$alkyl, alkyl includes unsubstituted alkyl and substituted alkyl, e.g. unsubstituted alkyl or alkyl substituted by one or more of
hydroxy; e.g. one or two,
halogen,
alkyloxycarbonyl, such as $(C_{1-6})$alkyloxycarbonyl; e.g. one,
alkylaminocarbonyl, such as $(C_{1-4})$alkylaminocarbonyl; e.g. one,
cycloalkyl, e.g. $(C_{3-8})$cycloalkyl, e.g. cyclohexyl; e.g. one,
aryl, e.g. $(C_{6-18})$aryl, e.g. phenyl; e.g. one,
heterocyclyl including a heterocyclic group comprising 3 to 7 ring members, preferably 5 to 6 ring members, and one to four, preferably 2, heteroatoms selected from N, O and S, preferably N, O, which heterocyclyl may be anellated with another ring/system, such as $(C_{6-18})$aryl, e.g. phenyl, such as imidazolyl, e.g. imidazol-2-yl, benzimidazolyl, e.g. benzimidazol-2-yl; e.g. one;
with the proviso that, in case of
14-O-[((Heterocyc-N-yl-cycloalkyl)-sulfanyl- or -oxy)-acetyl, -thioacetyl or -imino-oxy]-mutilins or 14-O-[((Heterocyc-N-yl-cycloalkyl)-alkylsulfanyl- or -alkyl-oxy)-acetyl, -thioacetyl or -imino-oxy]-mutilins, the heterocyclyl group is attached to cycloalkyl via a heterocyclic nitrogen atom.

A preferred compound according to the invention is a compound of general formula I

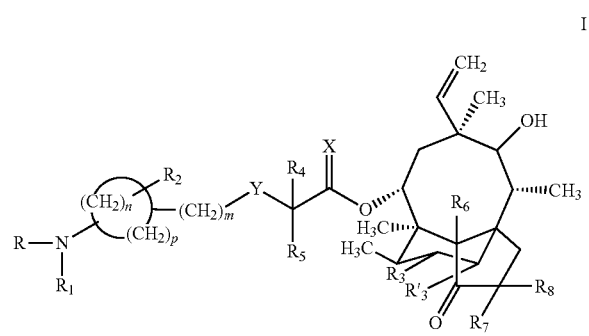

wherein
R is hydrogen or $(C_{1-8})$alkyl,
$R_1$ is
cycloalkyl including $(C_{3-12})$cycloalkyl, such as $(C_{4-8})$cycloalkyl, e.g. $(C_{5-7})$cycloalkyl,
unsubstituted $(C_{1-8})$alkyl, or
$(C_{1-8})$alkyl substituted by one or more of
hydroxy; preferably one or two,
halogen,
alkyloxycarbonyl, such as $(C_{1-6})$alkyloxycarbony; preferably one,
alkylaminocarbonyl, such as $(C_{1-4})$alkylaminocarbonyl; preferably one,
$(C_{3-8})$cycloalkyl, e.g. cyclohexyl; preferably one,
$(C_{6-18})$aryl, e.g. phenyl; preferably one,
heterocyclyl including a heterocyclic group comprising 3 to 7 ring members, preferably 5 to 6 ring members, and 1 to 4, preferably 2, heteroatoms selected from N, O and S, preferably N, O, which heterocyclyl may be anellated with another ring/system, such as $(C_{6-18})$ aryl, e.g. phenyl, such as imidazolyl, e.g. imidazol-2-yl, benzimidazolyl, e.g. benzimidazol-2-yl; preferably one,
X is sulphur, oxygen or $NR_{10}$, wherein $R_{10}$ is hydrogen or $(C_{1-8})$alkyl;
Y is sulphur or oxygen;
$R_2$ is hydrogen or one or more substituents, e.g. including substituents such as conventional in organic, e.g. (pleuro) mutilin, chemistry, e.g. $(C_{1-4})$alkyl, halogen;
$R_4$ and $R_5$ independently of each other are hydrogen or $(C_{1-8})$alkyl;
$R_3$ and $R_3'$ are hydrogen, deuterium or halogen;
$R_6$, $R_7$ and $R_8$ independently of each other are hydrogen, halogen or deuterium;
m is a number selected from 0 to 4,
n is a number selected from 0 to 10, and
p is a number selected from 0 to 10;
with the proviso that n plus p are at least 1, and preferably less than 13, such as 3 to 8, e.g. 3 to 5.

According to a preferred embodiment, in a compound of formula I,
R and $R_1$ are as defined above,
$R_2$ is hydrogen or $(C_{1-4})$alkyl;
$R_3$ is hydrogen,
$R_3'$ is hydrogen,
$R_4$ is hydrogen,
$R_5$ is hydrogen,
$R_6$ is hydrogen,
$R_7$ is hydrogen,
X is oxygen,
Y is sulphur,
m is a number selected from 0 to 4, more preferably m is 0,
n is a number selected from 0 to 8, more preferably from 0 to 7, such as 2 or 3,
p is a number selected from 0 to 8, more preferably from 0 to 7, such as 1,
with the proviso that n plus p are at least 2, and preferably less than 9; more preferably n plus p is 3 or 4;
e.g. wherein each single substituent defined may be a preferred substituent, independently from the other substituents defined.

A further preferred compound of the invention is a compound of formula $I_p$

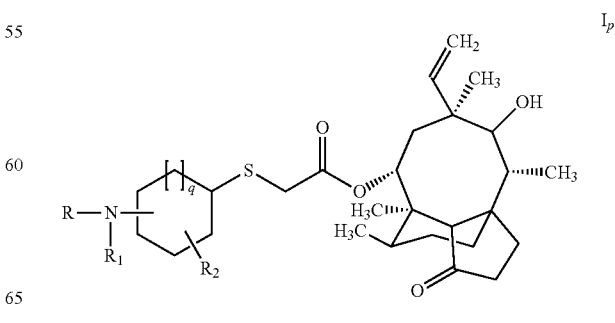

such as a compound of formula I$_{pp}$

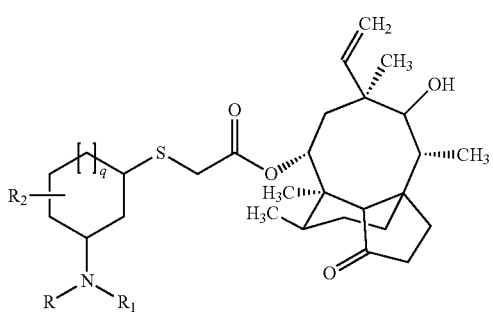

I$_{pp}$ wherein R and R$_1$ are as defined above,
R$_2$ is hydrogen or (C$_{1-4}$)alkyl, and
q is a number selected from 0, 1 and 2.

In formula I$_p$ a group —N(RR$_1$) may be in any position of the cycloalkyl ring system and is preferably in position 3 or in position 4, more preferably in position 3, e.g. as in a compound of formula I$_{pp}$.

According to a further preferred embodiment of the present invention, the compound is selected from the group consisting of 14-O-[(3-Diethylamino-cyclohexan-1-yl)-sulfanylacetyl]-mutilin, such as 14-O-[(3(R*)-Diethylamino-cyclohexan-1(S*)-yl)-sulfanylacetyl]-mutilin, and 14-O-[(3(R*)-Diethylamino-cyclohexan-1(R*)-yl)-sulfanylacetyl]-mutilin;

14-O-{[(3-Methylamino-cyclopent-1-yl)-sulfanyl]-acetyl}-mutilin, such as

14-O-{[(3(R/S)-Methylamino-cyclopent-1(R/S)-yl)-sulfanyl]-acetyl}-mutilin;

14-O-{[(3-Ethylamino-cyclopent-1-yl)-sulfanyl]-acetyl}-mutilin, such as

14-O-{[(3(R/S)-Ethylamino-cyclopent-1(R/S)-yl)-sulfanyl]-acetyl}-mutilin;

14-O-{[(3-Ethylamino-1-methyl-cyclopent-1-yl)-sulfanyl]-acetyl}-mutilin, such as 14-O-{[(3(R/S)-Ethylamino-1-methyl-cyclopent-1(R/S)-yl)-sulfanyl]-acetyl}-mutilin;

14-O-{[(3-Ethylamino-2-methyl-cyclopent-1-yl)-sulfanyl]-acetyl}-mutilin, such as 14-O-{[(3(R/S)-Ethylamino-2-methyl-cyclopent-1(R/S)-yl)-sulfanyl]-acetyl}-mutilin;

14-O-{[3-Ethylamino-cyclohexanylsulfanyl]-acetyl}-mutilin, such as

14-O-{[3(S)-Ethylamino-cyclohexan-1(R)-ylsulfanyl]-acetyl}-mutilin, and

14-O-{[3(R)-Ethylamino-cyclohexan-1(R)-ylsulfanyl]-acetyl}-mutilin;

14-O-{[3-(sec-Butylamino)-cyclopent-1-ylsulfanyl]-acetyl}-mutilin, such as

14-O-{[3(R/S)—((S)-sec-Butylamino)-cyclopent-1(R/S)-ylsulfanyl]-acetyl}-mutilin, and 14-O-{[3(R/S)—((R)-sec-Butylamino)-cyclopent-1(R/S)-ylsulfanyl]-acetyl}-mutilin;

14-O-[((3-(sec-Butylamino)-cyclohexan-1-yl)-sulfanyl)-acetyl]-mutilin, such as

14-O-[((3(S*)-(sec-(R)-Butylamino)-cyclohexan-1(R*)-yl)-sulfanyl)-acetyl]-mutilin, 14-O-[((3(S*)-(sec-(R)-Butylamino)-cyclohexan-1(S*)-yl)-sulfanyl)-acetyl]-mutilin, 14-O-[((3(S*)-(sec-(S)-Butylamino)-cyclohexan-1(S*)-yl)-sulfanyl)-acetyl]-mutilin, and 14-O-[((3(S*)-(sec-(S)-Butylamino)-cyclohexan-1(R*)-yl)-sulfanyl)-acetyl]-mutilin;

14-O-[((1-(sec-Butylamino)-cycloheptan-3-yl)-sulfanyl)-acetyl]-mutilin, such as

14-O-[((1-((R/S)-(sec-(R)-Butylamino)-cycloheptan-3(R/S)-yl)-sulfanyl)-acetyl]-mutilin;

14-O-{[3-(2,2,2-Trifluoro-ethylamino)-cyclopent-1-ylsulfanyl]-acetyl}-mutilin, such as 14-O-{[3(R/S)-(2,2,2-Trifluoro-ethylamino)-cyclopent-1(R/S)-ylsulfanyl]-acetyl}-mutilin;

14-O-{[3-(2,2,2-Trifluoro-ethylamino)-cyclohexan-1-ylsulfanyl]-acetyl}-mutilin, such as 14-O-{[3(R/S)-(2,2,2-Trifluoro-ethylamino)-cyclohexan-1(R/S)-ylsulfanyl]-acetyl}-mutilin;

14-O-{[3-(2,2-Difluoro-ethylamino)-cyclohexan-1-ylsulfanyl]-acetyl}-mutilin, such as 14-O-{[3(R/S)-(2,2-Difluoro-ethylamino)-cyclohexan-1(R/S)-ylsulfanyl]-acetyl}-mutilin, 14-O-{[(3-(2-Hydroxy-ethylamino)-cyclopent-1-yl)-sulfanyl]-acetyl}-mutilin, such as 14-O-{[(3(R/S)-(2-Hydroxy-ethylamino)-cyclopent-1(R/S)-yl)-sulfanyl]-acetyl}-mutilin;

14-O-{[3-(2-Hydroxy-propylamino)-cyclopent-1-ylsulfanyl]-acetyl}-mutilin, such as 14-O-{[3(R/S)-(2-(S)-Hydroxy-propylamino)-cyclopent-1(R/S)-ylsulfanyl]-acetyl}-mutilin, 14-O-{[3(R/S)-(2-(R)-Hydroxy-propylamino)-cyclopent-1(R/S)-ylsulfanyl]-acetyl}-mutilin, 14-O-[((3-(1-Isopropyl-2-hydroxy-ethylamino)-cyclopent-1-yl)-sulfanyl)-acetyl]-mutilin, such as 14-O-[((3(R/S)-(1(S)-Isopropyl-2-hydroxy-ethylamino)-cyclopent-1(R/S)-yl)-sulfanyl)-acetyl]-mutilin, 14-O-[((3-(1-Isopropyl-2-hydroxy-ethylamino)-cyclohexan-1-yl)-sulfanyl)-acetyl]-mutilin, such as 14-O-[((3(R/S)-(1(S)-Isopropyl-2-hydroxy-ethylamino)-cyclohexan-1(R/S)-yl)-sulfanyl)-acetyl]-mutilin;

14-O-{[3-(2-Hydroxy-1-hydroxymethyl-1-methyl-ethylamino)-eyclopent-1-ylsulfanyl]-acetyl}-mutilin, such as 14-O-{[3(R/S)-(2-Hydroxy-1-hydroxymethyl-1-methyl-ethylamino)-cyclopent-1(R/S)-ylsulfanyl]-acetyl}-mutilin;

14-O-{[3-(2-Hydroxy-1,1-bis-hydroxymethyl-ethylamino)-cyclopent-1-ylsulfanyl]-acetyl}-mutilin, such as 14-O-{[3(R/S)-(2-Hydroxy-1,1-bis-hydroxymethyl-ethylamino)-cyclopent-1(R/S)-ylsulfanyl]-acetyl}-mutilin;

14-O-[((3-(Methoxycarbonyl-methylamino)-cylopent-1-yl)-sulfanyl)-acetyl]-mutilin, such as 14-O-[((3(R/S)-(Methoxycarbonyl-methylamino)-cyclopent-1(R/S)-yl)-sulfanyl)-acetyl]-mutilin;

14-O-[((3-(Ethoxycarbonyl-methylamino)-cyclopent-1-yl)-sulfanyl)-acetyl]-mutilin, such as 14-O-[((3(R/S)-(Ethoxycarbonyl-methylamino)-cyclopent-1(R/S)-yl)-sulfanyl)-acetyl]-mutilin;

14-O-[(((3-(Isopropoxycarbonyl-methylamino)-cyclopent-1-yl)-sulfanyl)-acetyl]-mutilin, such as 14-O-[(((3(R/S)-(Isopropoxycarbonyl-methylamino)-cyclopent-1(R/S)-yl)-sulfanyl)-acetyl]-mutilin;

14-O-{[3-(Methoxypropynyl-2-amino)-cyclopent-1-yl-sulfanyl]-acetyl}-mutilin, such as 14-O-{[3(S*)-(Methoxypropynyl-2(S)-amino)-cyclopent-1(R/S)-yl-sulfanyl]-acetyl}-mutilin;

14-O-{[3-(Isopropoxypropynyl-2-amino)-cyclopent-1-yl-sulfanyl]-acetyl}-mutilin, such as 14-O-{[3(R*)-(Isopropoxypropionyl-2(S)-amino)-cyclopent-1(R*)-yl-sulfanyl]-acetyl}-mutilin,
14-O-{[3(R*)-(Isopropoxypropionyl-2(R)-amino)-cyclopent-1(R*)-yl-sulfanyl]-acetyl}-mutilin,
14-O-{[3(S*)-(Isopropoxypropionyl-2(R)-amino)-cyclopent-1(R*)-yl-sulfanyl]-acetyl}-mutilin, and
14-O-{[3(S*)-(Isopropoxypropionyl-2(S)-amino)-cyclopent-1(R*)-yl-sulfanyl]-acetyl}-mutilin;
14-O-{[(3-Methylcarbamoylmethylamino-cyclopent-1-yl)-sulfanyl]-acetyl}-mutilin, such as
14-O-{[(3(R/S)-Methylcarbamoylmethylamino-cyclopent-1(R/S)-yl)-sulfanyl]-acetyl}-mutilin,
14O-[(((3-(1-Cyclohexylethyl)-amino)-cyclohexan-1-yl)-sulfanyl)-acetyl]-mutilin, such as
14-O-[(((3-((1(R)-Cyclohexylethyl)-(S*)-amino)-cyclohexan-1(R*)-yl)-sulfanyl)-acetyl]-mutilin, and
14-O-[(((3-((1(R)-Cyclohexylethyl)-(S*)-amino)-cyclohexan-1(S*)-yl)-sulfanyl)-acetyl]-mutilin,
14-O-[(((3-(Phenylethyl)-amino)-cyclopentan-1-yl)-sulfanyl)-acetyl]-mutilin, such as
14-O-[(((3-((S)-Phenylethyl)-(R*)-amino)-cyclopentan-1(S*)-yl)-sulfanyl)-acetyl]-mutilin,
14-O-[(((3-((S)-Phenylethyl)-(S*)-amino)-cyclopentan-1(S*)-yl)-sulfanyl)-acetyl]-mutilin,
14-O-[(((3-((R)-Phenylethyl)-(R*)-amino)-cyclopentan-1(S*)-yl)-sulfanyl)-acetyl]-mutilin, and
14-O-[(((3-((R)-Phenylethyl)-(S*)-amino)-cyclopentan-1(S*)-yl)-sulfanyl)-acetyl]-mutilin,
14-O-[(((3-(Phenylethyl)-amino)-cyclohexan-1-yl)-sulfanyl)-acetyl]-mutilin, such as
14-O-[(((3(R*)-((S)-Phenylethyl)-amino)-cyclohexan-1(R*)-yl)-sulfanyl)-acetyl]-mutilin,
14-O-[(((3(S*)-((S)-Phenylethyl)-amino)-cyclohexan-1(R*)-yl)-sulfanyl)-acetyl]-mutilin,
14-O-[(((3(S*)-((R)-Phenylethyl)-amino)-cyclohexan-1(R*)-yl)-sulfanyl)-acetyl]-mutilin,
14-O-[(((3(R*)-((R)-Phenylethyl)-amino)-cyclohexan-1(R*)-yl)-sulfanyl)-acetyl]-mutilin,
14-O-[(((3(R*)-((R)-Phenylethyl)-amino)-cyclohexan-1(S*)-yl)-sulfanyl)-acetyl]-mutilin, and
14-O-[(((3(S*)-((R)-Phenylethyl)-amino)-cyclohexan-1(S*)-yl)-sulfanyl-acetyl]-mutilin;
14-O-{[3-(1H-Benzoimidazol-2-ylmethylamino)-cyclopent-1-ylsulfanyl]-acetyl}-mutilin, such as
14-O-{[3(R/S)-(1H-Benzoimidazol-2-ylmethylamino)-cyclopent-1(R/S)-ylsulfanyl]-acetyl}-mutilin,
14-O-{[(3-Dimethylamino-cyclopent-1-yl)-sulfanyl]-acetyl}-mutilin, such as
14-O-{[(3(S*)-Dimethylamino-cyclopent-1(R*)-yl)-sulfanyl]-acetyl}-mutilin, and
14-O-{[(3(S*)-Dimethylamino-cyclopent-1(S*)-yl)-sulfanyl]-acetyl}-mutilin;
14-O-{[(3-Diethylamino-cyclopent-1)-yl)-sulfanyl]-acetyl}-mutilin, such as
14-O-{[(3(S*)-Diethylamino-cyclopent-1(S*)-yl)-sulfanyl]-acetyl}-mutilin, and
14-O-{[(3(S*)-Diethylamino-cyclopent-1(R*)-yl)-sulfanyl]-acetyl}-mutilin;
14-O-[((3-Diethylamino-cycloheptan-1-yl)-sulfanyl)-acetyl]-mutilin, such as
14-O-[((3(R/S)-Diethylamino-cycloheptan-1(R/S)-yl)-sulfanyl)-acetyl]-mutilin;
14-O-{[(3-Cyclopropylamino-cyclopent-1-yl)-sulfanyl]-acetyl}-mutilin, such as
14-O-{[(3(R/S)-Cyclopropylamino-cyclopent-1(R/S)-yl)-sulfanyl]-acetyl}-mutilin,
14-O-{[(3-Cyclopropylamino-cyclohexan-1-yl)-sulfanyl]-acetyl}-mutilin, such as
14-O-{[(3 (S)-Cyclopropylamino-cyclohexan-1(R)-yl)-sulfanyl]-acetyl}-mutilin, and
14-O-{[(3(R)-Cyclopropylamino-cyclohexan-1(R)-yl)-sulfanyl]-acetyl}-mutilin;
14-O-[((3-(Morpholin-4-yl)-cyclohexan-1-yl)-sulfanyl)-acetyl]-mutilin, such as
14-O-[((3(R*)-(Morpholin-4-yl)-cyclohexan-1(S*)-yl)-sulfanyl)-acetyl]-mutilin, and
14-O-[((3(R*)-(Morpholin-4-yl)-cyclohexan-1(R*)-yl)-sulfanyl)-acetyl]-mutilin;
14-O-{[(3-(1H-Imidazol-2-ylamino)-cyclopent-1-yl)-sulfanyl]-acetyl}-mutilin, such as
14-O-{[(3(R/S)-(1H-Imidazol-2-ylamino)-cyclopent-1(R/S)-yl)-sulfanyl]-acetyl}-mutilin; and
14-O-{[(3-(1H-Benzoimidazol-2-ylamino)-cyclopent-1-yl)-sulfanyl]-acetyl}-mutilin, such as
14-O-{[(3(R/S)-(1H-Benzoimidazol-2-ylamino)-cyclopent-1(R/S)-yl)-sulfanyl]-acetyl}-mutilin;
e.g. in the form of a salt, such as a hydrochloride.

A compound provided by the present invention is herein also designated as "compound(s) of (according to) the present invention". A compound of the present invention includes mutilin-14-yl acetic acid esters as defined above, including a compound of formula I, $I_p$ or $I_{pp}$. A compound of the present invention includes a compound in any form, e.g. in free form, in the form of a salt, in the form of a solvate and in the form of a salt and a solvate.

In another aspect the present invention provides a compound of the present invention in the form of a salt and/or solvate.

Such salts include preferably pharmaceutically acceptable salts, although pharmaceutically unacceptable salts are included, e.g. for preparation/isolation/purification purposes.

A salt of a compound of the present invention includes a base salt or an acid addition salt. Pharmaceutically acceptable base salts include ammonium salts such as a trimethylammonium salt, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine. Acid addition salts include salts of a compound of the present invention with an acid, e.g. hydrogen fumaric acid, fumaric acid, tartaric acid, ethane-1,2-disulphonic acid, maleic acid, naphthalin-1, 5-sulphonic acid, hydrochloric acid, deuterochloric acid, preferably hydrochloric acid.

A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of the present invention may exist in the form of isomers and mixtures thereof; e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racemates. Substituents at any asymmetric carbon atom may be present in the (R)-, (S)- or (R,S)-configuration, preferably in the (R)- or (S)-configuration.

For example, in a compound of formula $I_{pp}$ the carbon atom of the cycloalkyl ring which is attached to the side sulphur atom, and the carbon atom of the cycloalkyl ring to which the N(RR$_1$) group is attached, both are asymmetric carbon atoms. Substituents attached to such asymmetric carbon atom may thus exist in (R) and (S) configuration, including mixtures thereof. For example, if R$_2$ in a compound of formula I$_{pp}$ is other than hydrogen, the carbon atom to which R$_2$ is attached is an asymmetric carbon atom and R$_2$ thus may exist in (R) and (S) configuration, including mixtures thereof.

For example, if in a compound of formula I R$_1$ is substituted alkyl and that substituent is attached to a carbon atom of the side chain of such alkyl, the carbon atom to which such substituent is attached is an asymmetric carbon atom and such substituent may be in the (R)- and (S)-configuration, including mixtures thereof. The configuration of substituents attached to asymmetric carbon atoms of the mutilin-ring is preferably the same as in natural pleuromutilin.

Isomeric mixtures may be separated as appropriate, e.g. according, e.g. analogously, to a method as conventional, to obtain pure isomers. The present invention includes a compound of the present invention in any isomeric form and in any isomeric mixture. The present invention also includes tautomers of a compound of the present invention, where tautomers can exist.

Any compound described herein, e.g. a compound of the present invention and intermediates in their production may be prepared as appropriate, e.g. according, e.g. analogously, to a method as conventional, e.g. or as specified herein.

In another aspect the present invention provides a process for the preparation of 14-O-[((Mono- or dialkylamino)-cycloalkylsulfanyl- or -cycloalkyl-oxy)-acetyl, -thioacetyl or -imino-oxy]-mutilins; 14-O-[((Cycloalkyl- or heterocyclylamino)-cycloalkylsulfanyl- or -cycloalkyl-oxy)-acetyl, -thioacetyl or -imino-oxy]-mutilins; 14-O-[((Heterocyc-N-yl-cycloalkyl)-sulfanyl- or -oxy)-acetyl, -thioacetyl or -imino-oxy]-mutilins; 14-O[(((Mono- or dialkylamino)-cycloalkyl)-alkylsulfanyl- or alkyl-oxy)-acetyl, -thioacetyl or -imino-oxy]-mutilins; 14-O-[(((Cycloalkyl- or heterocyclylamino)-cycloalkyl)-alkylsulfanyl- or -alkyl-oxy)-acetyl, -thioacetyl or -imino-oxy]-mutilins; or 14-O-[((Heterocyc-N-yl-cycloalkyl)-alkylsulfanyl- or -alkyl-oxy)-acetyl, -thioacetyl or -imino-oxy]-mutilins, respectively, comprising
a. reacting a 14-O-[(Cycloalkanone-sulfanyl- or cycloalkanone-oxy)-acetyl, -thioacetyl or -imino-oxy]-mutilin or a 14-O-[(Cycloalkanone-alkylsulfanyl- or Cycloalkanone-alkyl-oxy)-acetyl, -thioacetyl or -imino-oxy]-mutilin, respectively, with an amine, e.g. including a heterocyclic amine comprising at least one nitrogen atom as a heteroatom, in the presence of titanium isopropoxide,
b. treating the mixture obtained with sodium cyano boronhydride in dry organic solvent, e.g. absolute ethanol, and adding water, and
c. isolating 14-O-[((Mono- or dialkylamino)-cycloalkylsulfanyl- or -cycloalkyl-oxy)-acetyl, -thioacetyl or -imino-oxy]-mutilins; 14-O-[((Cycloalkyl- or heterocyclylamino)-cycloalkylsulfanyl- or -cycloalkyl-oxy)-acetyl, -thioacetyl or -imino-oxy]-mutilins; 14-O-[((Heterocyc-N-yl-cycloalkyl)-sulfanyl- or -oxy)-acetyl, -thioacetyl or -imino-oxy]-mutilins; 14-O-[(((Mono- or dialkylamino)-cycloalkyl)-alkylsulfanyl- or -alkyl-oxy)-acetyl, -thioacetyl or -imino-oxy]-mutilins; 14-O-[(((Cycloalkyl- or heterocyclylamino)-cycloalkyl)-alkylsulfanyl- or -alkyl-oxy)-acetyl, -thioacetyl or -imino-oxy]-mutilins; or 14-O-[(((Heterocyc-N-yl-cycloalkyl)-alkylsulfanyl- or -alkyl-oxy)-acetyl, -thioacetyl or -imino-oxy]-mutilins, respectively, from the reaction mixture.

In another aspect the present invention provides a process for the preparation of a compound of formula I, comprising the following steps a. reacting a compound of formula II

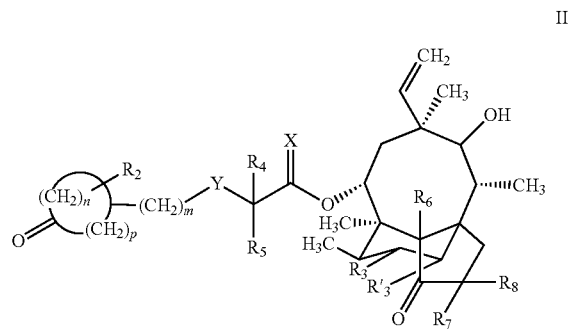

wherein X, Y, R$_2$, R$_3$, R'$_3$, R$_4$, R$_5$, R$_6$, R$_7$, R$_8$, n and p are as defined above, with an amine of formula —N(R)(R$_1$), wherein R and R$_1$ are as defined above, in the presence of titanium isopropoxide,
b. treating the mixture obtained in step a with sodium cyano boronhydride in dry organic solvent, e.g. absolute ethanol and adding water,
b. and isolating a compound of formula I, wherein X, Y, R, R$_1$, R$_2$, R$_3$, R'$_3$, R$_4$, R$_5$, R$_6$, R$_7$, R$_8$, n and p are as defined above, from the reaction mixture.

A 14-O-[(Cycloalkanone-sulfanyl- or cycloalkanone-oxy)-acetyl, -thioacetyl or -imino-oxy]-mutilin, e.g. a compound of formula II may be obtained as appropriate, e.g. according, e.g. analogously to a method as conventional, e.g. reacting a cycloalkanone with 14-O-[(Mercapto- or hydroxy)-acetyl, -thioacetyl or -imino-oxy]-mutilin, in the presence of an amine, e.g. triethylamine, and isolating a 14-O-[(Cycloalkanone-sulfanyl- or cycloalkanone-oxy)-acetyl, -thioacetyl or -imino-oxy]-mutilin, such as a compound of formula H, from the reaction mixture obtained.

A compound according to the present invention or an intermediate in the preparation of a compound of the present invention may e.g. also be obtained according, e.g. analogously, to a method as disclosed in WO0204414.

A compound obtained by a process provided by the present invention may be converted into a corresponding salt, according, e.g. analogously, to a method as conventional, e.g. by treatment with an acid, or, a base such as metal base or organic base, respectively, to obtain an acid addition salt, or, a base addition salt, respectively and vice versa. A compound obtained by a process provided by the present invention in the form of a salt may be converted into the corresponding compound in the form of a free base, according, e.g. analogously, to a method as conventional, e.g. by treatment with an acid if a base addition salt is obtained and by treating with a base if an acid addition salt is obtained.

The compounds of the present invention exhibit pharmacological activity and are therefore useful as pharmaceuticals.

For example, the compounds of the present invention show antimicrobial, e.g. antibacterial, activity against gram positive bacteria, such as coagulase positive Staphylococci, e.g. *Staphylococcus aureus*, coagulase negative Staphylococci, e.g. *Staphylococcus epidermidis, Staphylococcus haemolyticus*, and Streptococci, e.g. *Streptococcus pyogenes, Streptococcus pneumoniae*, Enterococci, e.g. *Enterococcus faecium*, and *Listeria monocytogenes*, and against gram negative bacteria such as *Moraxella*, e.g. *Moraxella catarrhalis*, and *Haemophilus*, e.g. *Haemophilus influenzae*, and *Legionella*, e.g. *Legionella pneumophila*, Neisseriaceae, e.g. *Neisseria gonorrhoeae*, as well as against Mycoplasms, *Chlamydia* and obligatory anaerobes, e.g. *Bacteroides fragilis, Clostridium difficile, Fusobacterium* spp., and *Propionibacterium* spp.

The in vitro activity against aerobic bacteria was determined by Agar Dilution Test or Microdilution Test according to the Clinical and Laboratory Standards Institute (CLSI, former NCCLS) Document M7-A7 Vol. 26, No. 2: "Methods for dilution Antimicrobial Susceptibility Tests for Bacteria that Grow Aerobically—Approved Standard; Seventh Edition (2006)"; and the test against anaerobic bacteria was performed according to the Clinical and Laboratory Standards Institute (CLSI, former NCCLS), Document, M11-A6, Vol. 24, No. 2: "Methods for Antimicrobial Susceptibility Testing of Anaerobic Bacteria—Approved Standard; Sixth Edition (2004)" and the in vivo activity was tested by the septicaemia mouse model against *Staphylococcus aureus.*

Compounds of the present invention are therefore suitable for the treatment and prevention of diseases which are mediated by microbes, e.g. by bacteria. Diseases which may also be treated include e.g. diseases mediated by *Helicobacter*, such as *Helicobacter pylori*, and diseases mediated by *Mycobacterium tuberculosis*. Diseases which may also be treated include in general inflammatory diseases, where microbes are mediating said inflammation, e.g. including acne.

In another aspect the present invention provides a compound of the present invention for use as a pharmaceutical, preferably as an antimicrobial, such as an antibiotic, e.g., and an anti-anaerobic.

In another aspect the present invention provides a compound of the present invention for use in acne treatment.

In a further aspect the present invention provides a compound of the present invention for use in the preparation of a medicament for the treatment of diseases, mediated by microbes, such as bacterials, for example diseases mediated by bacteria, e.g. selected from Staphylococci, Streptococci, Enterococci;

diseases mediated by bacteria, e.g. selected from *Moraxella, Haemophilus, Legionella, Neisseriaceae;* diseases mediated by *Helicobacter* diseases mediated by *Mycobacterium tuberculosis,* e.g. diseases mediated by Mycoplasms, *Chlamydia* and obligatory anaerobes, and for the treatment of acne.

In a further aspect the present invention provides a method of treatment of diseases mediated by microbes which comprises administering to a subject in need of such treatment an effective amount of a compound of the present invention, e.g. in the form of a pharmaceutical composition.

In a further aspect the present invention provides a method of treatment of acne which comprises administering to a subject in need of such treatment an effective amount of a compound of the present invention, e.g. in the form of a pharmaceutical composition.

Treatment includes treatment and prophylaxis.

For antimicrobial and acne treatment, the appropriate dosage will, of course, vary depending upon, for example, the chemical nature and the pharmakokinetic data of a compound of the present invention employed, the individual host, the mode of administration and the nature and severity of the conditions being treated. However, in general, for satisfactory results in larger mammals, for example humans, an indicated daily dosage is in the range from about 0.5 mg to 3 g of a compound of the present invention, conveniently administered, for example, in divided doses up to four times a day.

A compound of the present invention may be administered by any conventional route, for example enterally, e.g. including nasal, buccal, rectal, oral administration; parenterally, e.g. including intravenous, intramuscular, subcutaneous administration; or topically, e.g. including epicutaneous, intranasal, intratracheal administration, e.g. in form of coated or uncoated tablets, capsules, injectable solutions or suspensions, e.g. in the form of ampoules, vials, in the form of creams, gels, pastes, inhaler powder, foams, tinctures, lip sticks, drops, sprays, or in the form of suppositories, e.g. in analogous manner to macrolides, such as erythromycins, e.g. clarithromycin or azithromycin.

A compound of the present invention may be administered in the form of a pharmaceutically acceptable salt, e.g. an acid addition salt or metal salt; or in free form; optionally in the form of a solvate. A compound of the present invention in the form of a salt exhibits the same order of activity as the compound in free form; optionally in the form of a solvate.

A compound of the present invention may be used for pharmaceutical treatment according to the present invention alone or in combination with one or more other pharmaceutically active agents. Such other pharmaceutically active agents include e.g. other antibiotics and antiinflammatory agents, and, if a compound of the present invention is used in the treatment of acne, other pharmaceutically agents include furthermore agents which are active against acne.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention in free form or in the form of a pharmaceutically acceptable salt and/or in the form of a solvate in association with at least one pharmaceutical excipient, e.g. carrier or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

In another aspect the present invention provides a pharmaceutical composition according to the present invention, further comprising another pharmaceutically active agent.

Such pharmaceutical compositions may be manufactured according, e.g. analogously, to a method as conventional, e.g. by mixing, granulating, coating, dissolving or lyophilizing processes. Unit dosage form may contain, for example, from about 0.5 mg to about 1000 mg, such as 1 mg to about 100 mg.

The compounds of the present invention are additionally suitable as veterinary agents, e.g. veterinary active compounds, e.g. in the prophylaxis and in the treatment of microbial, e.g. bacterial diseases, in animals, such as fowl, pigs and calves, e.g., and for diluting fluids for artificial insemination and for egg-dipping techniques.

In another aspect the present invention provides a compound of the present invention for use as a veterinary agent.

In a further aspect the present invention provides a compound of the present invention for the preparation of a veterinary composition which is useful as a veterinary agent.

In another aspect the present invention provides a veterinary method for the prophylaxis and in the treatment of microbial, e.g. bacterial diseases which comprises administering to a subject in need of such treatment an effective amount of a compound of the present invention, e.g. in the form of a veterinary composition.

For use of the active compounds of the present invention as a veterinary agent, the dosage will of course vary depending upon the size and age of the animal and the effect desired; for example for prophylactic treatment relatively low doses would be administered over a longer time period, e.g. 1 to 3 weeks. Preferred doses in drinking water are from 0.0125 to 0.05 weight by volume, particularly 0.0125 to 0.025; and in foodstuffs from 20 to 400 g/metric ton, preferably 20 to 200 g/metric ton. It is preferred to administer the active compounds of the present invention as a veterinary agent to hens in drinking water, to pigs in foodstuff and to calves orally or parenterally, e.g. in the form of oral or parenteral preparations.

In the following examples all temperatures are in degrees Celsius (° C.) and are uncorrected.

EXAMPLE 1

14-O-[(3(R*)-Diethylamino-cyclohexan-1(S*)-yl)-sulfanylacetyl]-mutilin in the form of a hydrochloride and 14-O-[(3-(R*)-Diethylamino-cyclohexan-1-(R*)-yl)-sulfanylacetyl]-mutilin in the form of a hydrochloride

A. 14-O-Mercaptoacetyl-mutilin

A mixture of 15.2 g of thiourea and 106.4 g of pleuromutilin-22-O-tosylate in 250 ml of acetone is heated under reflux for 1.5 hours, from the mixture obtained solvent is evaporated and to the evaporation residue 100 ml of hexane are added. A precipitate forms and is isolated. To a solution of 12.2 g of the isolated precipitate in a mixture of 20 ml ethanol and 35 ml $H_2O$ (heated to 90°), a solution of 4.7 g of $Na_2S_2O_5$ in 25 ml of $H_2O$ and 100 ml of $CCl_4$ are added. The mixture obtained is heated under reflux for 2 hours, The organic phase is separated, dried, and solvent is evaporated to dryness. 14-O-Mercaptoacetyl-mutilin is obtained which may be used in further reaction steps without further purification. $^1$H-NMR ($CDCl_3$): ABX-system ($v_A$=3.15, $v_B$=3.22, $v_x$=1.92, 2H, $H_{22}$, J=15.8 Hz, J=8.2 Hz). MS m/e: 417 (M$^+$+Na).

B. 14-O-[(Cyclohexanone-3(R/S)-yl)-sulfanylacetyl]-mutilin

A mixture of 1.92 g of cyclohexenone, 7.88 g of 14-O-mercaptoacetylmutilin and 0.5 ml of triethylamine is stirred in pyridine at 25° for 15 hours. To the mixture obtained ethyl acetate is added and the mixture obtained is extracted with 1N HCl and repeatedly washed with brine. From the organic phase solvent is evaporated (to dryness). 14-O-[(Cyclohexanone-3(R/S)-yl)-sulfanylacetyl]-mutilin is obtained which may be used in further reaction steps without further purification. $^1$H-NMR ($CDCl_3$)): 3.22 (m, 1H, SCH), AB-system: ($v_A$=3.29, $v_B$=3.37, 2H, $H_{22}$, J=14.8 Hz). MS m/e: 513 (M$^+$+Na).

B1. 14-O-[(Cycloheptanone-3(R/S)-yl)-sulfanylacetyl]-mutilin is prepared analogously to the method of Example 1, step B., but using appropriate starting materials. $^1$H-NMR ($d_6$-DMSO): AB-system: ($v_A$=3.32, $v_B$=3.22, 2H, $H_{22}$, J=14.8 Hz), 3.15 (m, 1H, SCH), AB-system: ($v_A$=2.75, $v_B$=2.62, 2H, COCH$_2$CHS, J=14 Hz). 14-O-[(Cycloheptanone-3(R/S)-yl)-sulfanylacetyl]-mutilin is not used in Example 1 but as a starting material in other examples.

B2. 14-O-[(Cyclopentanone-3(R/S)-yl)-sulfanylacetyl]-mutilin is prepared analogously to the method of Example 1, step B., but using appropriate starting materials. $^1$H-NMR ($CDCl_3$)): 3.6 (m, 1H, SCH), AB-system: ($v_A$=3.25, $v_B$=3.17, 2H, $H_{22}$, J=14.8 Hz), AB-system: ($v_A$=2.55, $v_B$=2.2, 2xm, 2H, CHCH$_2$CO). 14-O-[(Cyclopentanone-3(R/S)-yl)-sulfanylacetyl]-mutilin is not used in Example 1 but as a starting material in other examples.

C. 14-O-[(3(R*)-Diethylamino-cyclohexan-1(S*)-yl)-sulfanylacetyl]-mutilin in the form of a hydrochloride and 14-O-[(3-(R*)-Diethylamino-cyclohexan-1-(R*)-yl)-sulfanylacetyl]-mutilin in the form of a hydrochloride A mixture of 5.39 g of 14-O-[(Cyclohexanone-3(R/S)-yl)-sulfanylacetyl]-mutilin, 803 mg of diethyl amine and 3.9 g of titanium(IV) isopropoxide is stirred at 25° for 1 to 8 hours, then 456 mg of sodium cyano boronhydride and 10 ml absolute ethanol are added. The reaction mixture is kept at 25° for 3 hours. 10 ml of water are added and the mixture obtained is extracted with acetic acid ethyl ester. The organic phase is dried and solvent is evaporated to dryness. The evaporation residue is subjected to chromatography on silica gel (EE/MeOH 1:1) to yield 1.58 g of 14-O-[(3(R*)-Diethylamino-cyclohexan-1(S*)-yl)-sulfanylacetyl]-mutilin and 2.81 g of 14-O-[(3-(R*)-Diethylamino-cyclohexan-1-(R*)-yl)-sulfanylacetyl]-mutilin. Hydrochlorides of 14-O-[(3(R*)-Diethylamino-cyclohexan-1(S*)-yl)-sulfanylacetyl]-mutilin and 14-O-[(3-(R*)-Diethylamino-cyclohexan-1-(R*)-yl)-sulfanylacetyl]-mutilin are obtained by treating the free amines with 0.1 N HCl in ether.

Analogously to a method as set out in Example 1, but using appropriate starting materials, a compound of formula EX

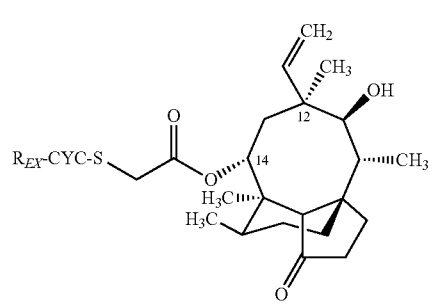

EX wherein CYC and $R_{EX}$ are as defined in TABLE 1 below are obtained.

TABLE 1

| EX | $R_{EX}$ | CYC | DATA |
|---|---|---|---|
| 1a | H$_3$C—\\N— / H$_3$C— | C6 | 14-O-[(3(R*)-Diethylamino-cyclohexan-1(S*)-yl)-sulfanylacetyl]-mutilin: 10.05 (b, 1H, NH$^+$), 6.15 (dd, 1H, H$_{19}$, J = 17.6 Hz, J = 11.2 Hz), 5.6 (d, 1H, H$_{14}$, J = 8.2 Hz), 5.05 (m, 2H, H$_{20}$), AB-System: $v_A$ = 3.44, $v_B$ = 3.33 (2H, SCH$_2$, J = 14.9 Hz), 3.05, 3.2 (2xb, 5H, NCH$_2$, NCH), 2.8 (b, 1H, SCH), 2.4 (b, 1H, H$_4$), 1.34 (s, 3H, (CH$_3$)$_{15}$), 1.25 (t, 6H, NCH$_2$CH$_3$, J = 8.2 Hz), 1.05 (s, 1H, (CH$_3$)$_{18}$), 0.81 (d, 3H, (CH$_3$)$_{17}$, J = 6.9 Hz), 0.63 (m, 3H, (CH$_3$)$_{16}$). MS m/e: 548 (MH$^+$). |
| 1b | | | 14-O-[(3(R*)-Diethylamino-cyclohexan-1(R*)- |

TABLE 1-continued

| EX | R_{EX} | CYC | DATA |
|---|---|---|---|
| | | | yl)-sulfanylacetyl]-mutilin: 9.5 (b, 1H, NH$^+$), 3.35 (m, 2H, H$_{22}$,) 3.05, 3.18 (2xb, 5H, NCH$_2$, NCH), 1.25 (t, 6H, NCH$_2$CH$_3$, J = 8.2 Hz), MS m/e: 548 (MH$^+$) |
| 2 | H$_3$C-NH-CH$_3$ | C5 | 14-O-{[(3(R/S)-Methylamino-cyclopent-1(R/S)-yl)-sulfanyl]-acetyl}-mutilin: 8.8 (b, 2H, NH$_2$$^+$), 3.55 (m, 1H, NCH)), 3.15 (m, 1H, SCH), MS m/e: 492 (M$^+$) |
| 3 | H$_3$C-CH$_2$-NH-CH$_3$ | C5 | 14-O-{[(3(R/S)-Ethylamino-cyclopent-1(R/S)-yl)-sulfanyl]-acetyl}-mutilin: 8.8 (b, 2H, NH$_2$$^+$), 3.55, 3.35 (2xm, 1H, NCH)), 3.15 (m, 1H, SCH), 2.88 (q, 2H, NCH$_2$CH$_3$, J = 7.2 Hz), 1.18 (t, 3H, CH$_2$CH$_3$, J = 7.2 Hz), MS m/e: 506 (MH$^+$) |
| 4 | H$_3$C-CH$_2$-NH-CH$_3$ | 1-methyl-cyclopentyl (CH$_3$ at position 1) | 14-O-{[(3(R/S)-Ethylamino-1-methyl-cyclopent-1(R/S)-yl)-sulfanyl-acetyl}-mutilin: 8.8 (b, 2H, (NH$_2$)$^+$), 3.6 (m, 1H, NCH), 2.9 (m, 2H, NCH$_2$), 3.35 (m, 2H, H$_{22}$), 1.3 (s, 3H, SCCH$_3$), MS m/e: 520 (MH$^+$) |
| 5 | H$_3$C-CH$_2$-NH-CH$_3$ | 2-methyl-cyclopentyl (CH$_3$ at position 2) | 14-O-{[(3(R/S)-Ethylamino-2-methyl-cyclopent-1(R/S)-yl)-sulfanyl-acetyl}-mutilin: 8.3-8.9 (b, 2H, (NH$_2$)$^+$), 2.7, 2.85, 3.1 (3xm, 4H, SCH, NCH, NCH$_2$), 3.35 (m, 2H, H$_{22}$), 1.2 (m, 6H, NCH, CH$_3$, CCH$_3$), MS m/e: 520 (MH$^+$) |
| 6a | H$_3$C-CH$_2$-NH-CH$_3$ | C6 | 14-O-{[3-Ethylamino-cyclohexylsulfanyl]-acetyl}-mutilin: 8.6 (b, 2H, NH$_2$$^+$), 3.3 (m, 4H, NCH$_2$CH$_3$, H$_{22}$), 2.95 (m, 2H, NCH, SCH), 1.18 (t, 3H, CH$_3$CH$_2$), MS m/e: 520 (MH$^+$) |
| 6b | | | 14-O-{[3(S)-Ethylamino-cyclohex-1(R)-ylsulfanyl]-acetyl}-mutilin + 1S3R-Diastereomer: 8.65 (b, 2H, NH$_2$$^+$), 3.35 (m, 2H, H$_{22}$), 2.95, 2.75 (2xm, 3H, NCH$_2$CH$_3$, NCH, SCH), 1.18 (t, 3H, NCH$_2$CH$_3$), MS m/e: 520 (MH$^+$) |
| 6c | | | 14-O-{[3(R)-Ethylamino-cyclohex-1(R)-ylsulfanyl]-acetyl}-mutilin + 1S3S-Diastereomer: 8.6 (b, 2H, NH$_2$$^+$), 3.40-3.15 (m, 4H, H$_{22}$, NCH, SCH), 2.93 (q, 2H, NCH$_2$CH$_3$), 1.17 (t, 3H, NCH$_2$CH$_3$), MS m/e: 520 (MH$^+$) |
| 7a | H$_3$C-CH(C$_2$H$_5$)-NH-CH$_3$ | C5 | 14-O-{[3-(R/S)-((S)-sec-Butylamino)-cyclopent-1(R/S)-ylsulfanyl]-acetyl}-mutilin: 8.75, 8.6 (2xb, 2H, NH$_2$$^+$), 3.15, 3.6 (2xb, 2H, NCH, NCHCH$_3$), 3.05 (b, 1H, SCH), 1.18 (d, 3H, CH$_3$CH, 4.4 Hz), 0.88 (t, 3H, CH$_3$CH$_2$), MS m/e: 534 (MH$^+$) |
| 7b | | | 14-O-{[3-(R/S)-((R)-sec-Butylamino)-cyclopent-1(R/S)-ylsulfanyl]-acetyl}-mutilin: 8.85, 8.65 (2xb, 2H, NH$_2$$^+$), 3.15, 3.6, 3.7 (3xb, 2H, NCH, NCHCH$_3$), 3.3 (m, 2H, H$_{22}$), 3.02 (b, 1H, SCH), 1.18 (m, 3H, CH$_3$CH) 0.88 (t, 3H, CH$_3$CH$_2$), MS m/e: 534 (MH$^+$) |
| 8a | H$_3$C-CH(C$_2$H$_5$)-NH-CH$_3$ | C6 | 14-O-[(3-(S*)-(sec-(R)-Butylamino)-cyclohexan-1-(R*)-yl)-sulfanyl)-acetyl]-mutilin: 3.3 (b, 2H, NH$_2$$^+$), 3.3 (m, 2H, H$_{22}$) 3.1, 3.2 (2xb, 2H, 2 x NCH), 2.75 (b, 1H, SCH), 1.18 (d, 3H, CH$_3$CH, 4.4 Hz), 0.9 (t, 3H, CH$_3$CH$_2$, J = 8.4 Hz) |
| 8b | | | 14-O-[(3-(S*)-(sec-(R)-Butylamino)-cyclohexan-1-(S*)-yl)-sulfanyl-acetyl]-mutilin: 8.55 (b, 2H, NH$_2$$^+$), 3.4 (m, 2H, H$_{22}$) 3.15 (b, 1H, SCH), 1.18 (d, 3H, CH$_3$CH, 4.4 Hz), 0.9 (t, 3H, CH$_3$CH$_2$, J = 8.4 Hz) |
| 8c | | | 14-O-[(3-(S*)-(sec-(S)-Butylamino)-cyclohexan-1-(S*)-yl)-sulfanyl-acetyl]-mutilin: 8.45, (b, 2H, NH$_2$$^+$), 3.4 (m, 2H, H$_{22}$) 3.05 (b, 1H, SCH), 3.2 (b, 1H, NCH), 1.18 (d, 3H, CH$_3$CH, 4.4 Hz), 0.9 (t, 3H, CH$_3$CH$_2$, J = 8.4 Hz) |
| 8d | | | 14-O-[(3-(S*)-(sec-(S)-Butylamino)-cyclohexan-1-(R*)-yl)-sulfanyl-acetyl]-mutilin: 8.45, 8.55 (2xb, 2H, NH$_2$$^+$), AB-system (v$_A$ = 3.35, v$_B$ = 3.42, H$_{22}$, J = 14.5 Hz), 3.15 (b, 1H, SCH), 1.18 (d, 3H, CH$_3$CH, 4.4 Hz), 0.9 (t, 3H, CH$_3$CH$_2$, J = 8.4 Hz) |

TABLE 1-continued

| EX | R_EX | CYC | DATA |
|---|---|---|---|
| 9 | H₃C-CH(NHCH₃)-CH₂-CH₃ (sec-butyl-N-methylamine structure) | C7 | 14-O-[1-((R/S)-(sec-(R)-Butylamino)-cycloheptane-3(R/S)-yl)-sulfanyl-acetyl}-mutilin: 8.65, 8.55 (2xb, 2H, NH$_2^+$), 3.4-3.45 (m, 3H, H$_{11}$, H$_{22}$), 2.9 (b, 1H, SCH), 3.1-3.3 (m, 3H, NCH, NCHCH$_3$), 1.18 (d, 3H, CH$_3$CH, 4.4 Hz), 0.9 (m, 3H, CH$_3$CH$_2$) |
| 10 | F$_3$C-CH$_2$-NH-CH$_3$ | C5 | 14-O-{[3(R/S)-(2,2,2-Trifluoro-ethylamino)-cyclopent-1(R/S)-ylsulfanyl]-acetyl}-mutilin: 9.9 (b, 2H, (NH$_2$)$^+$), 3.55, 3.7, 4.0 (3xb, 3H, NCH$_2$, NCH), 3.3 (m, 2H, H$_{22}$), 3.1 (m, 1H, SCH) |
| 11 | F$_3$C-CH$_2$-NH-CH$_3$ | C6 | 14-O-{[3(R/S)-(2,2,2-Trifluoro-ethylamino)-cyclohexan-1(R/S)-ylsulfanyl]-acetyl}-mutilin: 3.1-3.3 (m, 5H, H$_{22}$, NCH$_2$CF$_3$), 2.35, 2.65, 2.78 (3xm, 2H, NCH, SCH), MS m/e: 574 (MH$^+$), 596 (MNa$^+$) |
| 12 | F$_2$HC-CH$_2$-NH-CH$_3$ | C6 | 14-O-{[3(R/S)-(2,2-Difluoro-ethylamino)-cyclohexan-1(R/S)-ylsulfanyl]-acetyl}-mutilin: 5.7-6.05 (m, 1H, NCH$_2$CHF$_2$), 3.1-3.3 (m, 2H, H$_{22}$), 2.85 (m, 2H, NCH$_2$CHF$_2$), 2.35, 2.65, 2.74 (3xm, 2H, NCH, SCH), MS m/e: 556 (MH$^+$), 578 (MNa$^+$) |
| 13 | HO-CH$_2$-CH$_2$-NH-CH$_3$ | C5 | 14-O-{[3(R/S)-(2-Hydroxy-ethylamino)-cyclopent-1(R/S)-yl)-sulfanyl]-acetyl}-mutilin: 8.2-8.7 (b, 2H, (NH$_2$)$^+$), 5.15 (b, 1H, CH$_2$OH), 3.6 (m, 2H, CH$_2$OH), 3.3 (m, 2H, H$_{22}$), 3.1 (m, 1H, SCH), 2.9 (m, 2H, NCH$_2$CH$_2$OH), MS m/e: 522 (MH$^+$) |
| 14a | H$_3$C-CH(OH)-CH$_2$-NH-CH$_3$ | C5 | 14-O-{[3-(R/S)-(2-(S)-Hydroxy-propylamino)-cyclopent-1(R/S)-ylsulfanyl]-acetyl}-mutilin: 8.5-8.9 (2xb, 2H, (NH$_2$)$^+$), 5.3 (d, 1H, OH, J = 4.4 Hz), 3.3 (m, 2H, H$_{22}$), 3.9 (m, 1H, CHOH), AB-system (v$_A$ = 2.9, v$_B$ = 2.7, 2H, NCH$_2$CH), 3.1 (m, 1H, SCH), 2.4 (m, 1H, NCH), 1.1 (d, 3H, CHCH$_3$) |
| 14b | | | 14-O-{[3-(R/S)-(2-(R)-Hydroxy-propylamino)-cyclopent-1(R/S)-ylsulfanyl]-acetyl}-mutilin: 8.6-8.75 (2xb, 2H, (NH$_2$)$^+$), 3.3 (m, 2H, H$_{22}$), 3.9 (m, 1H, CHOH), AB-system (v$_A$ = 2.9, v$_B$ = 2.7, 2H, NCH$_2$CH), 3.1 (m, 1H, SCH), 2.4 (m, 1H, NCH), 1.1 (d, 3H, CHCH$_3$) |
| 15 | HO-CH$_2$-CH(iPr)-NH-CH$_3$ (isopropyl + hydroxymethyl branched) | C5 | 14-O-[((3(R/S)-(1(S)-Isopropyl-2-hydroxy-ethylamino)-cyclopent-1(R/S)-yl)-sulfanyl)-acetyl]-mutilin: 8.35, 8.75 (2xb, 2H, (NH$_2$)$^+$), 5.3 (b, 1H, OH), 3.55-3.7 (b, 2H, OCH$_2$), 2.9, 3.0, 3.3 (3xb, 2xNCH, SCH), 3.25 (m, 2H, H$_{22}$), 1.0 (m, 6H, CH(CH$_3$)$_2$), MS m/e: 550 (MH$^+$). |
| 16 | HO-CH$_2$-CH(iPr)-NH-CH$_3$ | C6 | 14-O-[((3-(R/S)-(1(S)-Isopropyl-2-hydroxy-ethyl-amino)-cyclohexan-1-(R/S)-yl)-sulfanyl)-acetyl]-mutilin: 8.05, 8.35 (2xb, 2H, NH$_2^+$), 5.3 (b, 1H, OH), 3.65 (b, 2H, CH$_2$OH), AB-system (v$_A$ = 3.35, v$_B$ = 3.42, H$_{22}$, J = 14.5 Hz), 3.18 (b, 2H, NCHCH$_2$, NCH), 2.7 (b, 1H, SCH), 1.18 (d, 3H, CH$_3$CH, 4.4 Hz), 0.9, 1.0 (2xd, 6H, (CH$_3$)$_2$CH, J = 6.7 Hz). |
| 17 | (HOCH$_2$)(H$_3$C)C(CH$_2$OH)-NH-CH$_3$ | C5 | 14-O-{[3(R/S)-(2-Hydroxy-1-hydroxymethyl-1-methyl-ethylamino)-cyclopent-1(R/S)-ylsulfanyl]-acetyl}-mutilin: 4.25 (b, 2H, OH), 3.25 (m, 1H, NCH), 3.3 (m, 2H, H$_{22}$), 3.12 (s, 4H, CH$_2$OH), 3.05 (b, 1H, SCH), 0.85 (s, 3H, CCH$_3$) |
| 18 | (HOCH$_2$)$_2$C(CH$_2$OH)-NH-CH$_3$ | C5 | 14-O-{[3(R/S)-(2-Hydroxy-1,1-bis-hydroxymethyl-ethylamino)-cyclopent-1(R/S)-ylsulfanyl]-acetyl}-mutilin: 8.2 (b, 2H, (NH$_2$)$^+$), 3.6 (s, 6H, CH$_2$OH), 3.3 (m, 2H, H$_{22}$), 3.1 (m, 1H, SCH), MS m/e: 582 (MH$^+$) |
| 19 | CH$_3$O-C(=O)-CH$_2$-NH-CH$_3$ | C5 | 14-O-[((3(R/S)-(Methoxycarbonylmethyl-amino)-cyclopent-1(R/S)-yl)-sulfanyl)-acetyl]-mutilin: 9.38 (b, 1H, (NH$_2$)$^+$), 3.98 (bs, 2H, COCH$_2$N), 3.72 (s, 3H, OCH$_3$), 3.25 (m, 2H, H$_{22}$) 3.12, 3.44, 3.62 (3xm, 2H, NCH, SCH), MS m/e: 550 (MH$^+$) |

TABLE 1-continued

| EX | R$_{EX}$ | CYC | DATA |
|---|---|---|---|
| 20 | (structure) | C5 | 14-O-[(((3(R/S)-(Ethoxycarbonylmethyl-amino)-cyclopent-1(R/S)-yl)-sulfanyl)-acetyl]-mutilin: 9.35 (b, 1H, (NH$_2$)$^+$), 4.2 (q, 2H, OCH$_2$CH$_3$, J = 6.8 Hz), 3.95 (s, 2H, COCH$_2$N), 3.98b, 1H, NHCH$_2$), 3.25 (m, 2H, H$_{22}$) 3.12, 3.44, 3.62 (3xm, 2H, NCH, SCH), 1.25 (t, 3H, OCH$_2$CH$_3$), J = 6.8 Hz), MS m/e: 564 (MH$^+$) |
| 21 | (structure) | C5 | 14-O-[((3(R/S)-(Isopropoxycarbonyl-methyl-amino)-cyclopent-1(R/S)-yl)-sulfanyl)-acetyl]-mutilin: 9.35 (2xb, 2H, (NH$_2$)$^+$), 3.98b, 1H, NHCH$_2$), 3.25 (m, 2H, H$_{22}$, J = 14.5 Hz), 3.15, 3.45, 3.6 (3xm, 2H, NCH, SCH), 1.25 (d, 6H, OCH(CH$_3$)$_2$, J = 6.5 Hz), MS m/e: 578 (MH$^+$) |
| 22 | (structure) | C5 | 14-O-{[3(S*)-(Methoxypropionyl-2(S)-amino)-cyclopent-1(R*)-yl-sulfanyl]-acetyl}-mutilin: 9.3, 9.55 (2xb, 2H, NH$_2^+$), 4.1 (m, 1H, NCHCH$_3$), 3.55 (m, 1H, NCH)), 3.75 (s, 3H, OCH$_3$), 3.12 (m, 1H, SCH), MS m/e: 564 (M$^+$). |
| 23a | (structure) | C5 | 14-O-{[3(R*)-(Isopropoxypropionyl-2(S)-amino)-cyclopent-1(R*)-yl-sulfanyl]-acetyl}-mutilin + 1S*3S*Diastereomer: 9.25, 9.6 (2xb, 2H, (NH$_2$)$^+$), 5.05 (m, 3H, COOCH, H$_{20}$), 4.05 (b, 1H, COCHN), 3.65 (m, 1H, NCH), 3.3 (m, 2H, H$_{22}$), 1.25 (m, 6H, OCH(CH$_3$)$_2$), 1.45 (d, 3H, NCHCH$_3$), MS m/e: 592 (MH$^+$) |
| 23b |  |  | 14-O-{[3(R*)-(Isopropoxypropionyl-2(R)-amino)-cyclopent-1(R*)-yl-sulfanyl]-acetyl}-mutilin + 1S*3S*Diastereomer: 9.25, 9.55 (2xb, 2H, (NH$_2$)$^+$), 5.05 (m, 3H, COOCH, H$_{20}$), 4.05 (b, 1H, COCHN), 3.65 (m, 1H, NCH), 3.3 (m, 2H, H$_{22}$), 1.25 (m, 6H, OCH(CH$_3$)$_2$), 1.45 (d, 3H, NCHCH$_3$), MS m/e: 592 (MH$^+$) |
| 23c |  |  | 14-O-{[3(S*)-(Isopropoxypropionyl-2(R)-amino)-cyclopent-1(R*)-yl-sulfanyl]-acetyl}-mutilin + 1S*3R*Diastereomer: 9.3, 9.6 (2xb, 2H, (NH$_2$)$^+$), 5.05 (m, 3H, COOCH, H$_{20}$), 4.0 (b, 1H, COCHN), 3.3 (m, 2H, H$_{22}$), 3.15 (b, 1H, SCH), 1.25 (m, 6H, OCH(CH$_3$)$_2$), 1.45 (d, 3H, NCHCH$_3$), MS m/e: 592 (MH$^+$) |
| 23d |  |  | 14-O-{[3(S*)-(Isopropoxypropionyl-2(S)-amino)-cyclopent-1(R*)-yl-sulfanyl]-acetyl}-mutilin + 1S*3R*Diastereomer: 9.3, 9.6 (2xb, 2H, (NH$_2$)$^+$), 4.95 (m, 3H, COOCH, H$_{20}$), 4.0 (b, 1H, COCHN), 3.3 (m, 2H, H$_{22}$), 3.15 (b, 1H, SCH), 1.25 (m, 6H, OCH(CH$_3$)$_2$), 1.45 (d, 3H, NCHCH$_3$), MS m/e: 592 (MH$^+$) |
| 24 | (structure) | C5 | 14-O-{[[(3(R/S)-Methylcarbamoylmethyl-amino-cyclopent-1(R/S)-yl)-sulfanyl]-acetyl}-mutilin: 9.1, 8.4 (2xb, 3H, NH, (NH$_2$)$^+$), 3.6 (bs, 2H, COCH$_2$N), 3.1 (b, 1H, SCH), 2.62 (d, 3H, NCH$_3$, J = 4.6 Hz), MS m/e: 549 (MH$^+$) |
| 25a | (structure) | C6 | 14-O-[((3-((1-(R)-Cyclohexyl-ethyl)-(S)-amino)-cyclohexan-1-(R)-yl)-sulfanyl)-acetyl]-mutilin + RS-Diastereomeres: 8.05, 8.45 (2xb, 2H, NH$_2^+$), AB-system (v$_A$ = 3.35, v$_B$ = 3.42, H$_{22}$, J = 14.5 Hz), 3.05, 3.2 (2xb, 2H, NCHCH3, NCH), 2.75 (b, 1H, SCH), 1.18 (d, 3H, CH$_3$CH, 4.4 Hz) |
| 25b |  |  | 14-O-[((3-((1(R)-Cyclohexyl-ethyl)-(S)-amino)-cyclohexan-1-(S)-yl)-sulfanyl)-acetyl]-mutilin + SS-Diastereomeres: 8.05, 8.45 (2xb, 2H, NH$_2^+$), AB-system (v$_A$ = 3.35, v$_B$ = 3.42, H$_{22}$, J = 14.5 Hz), 3.18 (b, 1H, SCH), 1.18 (d, 3H, CH$_3$CH, 4.4 Hz |
| 25c |  |  | 14-O-[((3-((1-(R)-Cyclohexyl-ethyl)-(S*)-amino)-cyclohexan-1-(R*)-yl)-sulfanyl)-acetyl]-mutilin: 8.15, 8.55 (2xb, 2H, NH$_2^+$), AB-system (v$_A$ = |

TABLE 1-continued

| EX | R_EX | CYC | DATA |
|---|---|---|---|
| | | | 3.35, $v_B$ = 3.42, $H_{22}$, J = 14.5 Hz), 3.18, 3.05 (b, 2H, NCHCH$_2$, NCH), 2.75 (b, 1H, SCH), 1.12 (d, 3H, CH$_3$CH, 4.4 Hz) |
| 25d | | | 14-O-[((3-((1(R)-Cyclohexyl-ethyl)-(S*)-amino)-cyclohexan-1-(S*)-yl)-sulfanyl)-acetyl]-mutilin: 8.35, 8.65 (2xb, 2H, NH$_2$$^+$), AB-system ($v_A$ = 3.38, $v_B$ = 3.28, $H_{22}$, J = 14.5 Hz), 3.25 (b, 1H, NCHCH$_2$), 3.15 (b, 1H, SCH), 1.2 (d, 3H, CH$_3$CH, 4.4 Hz) |
| 26a | 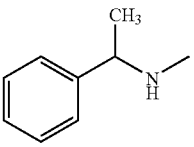 | C5 | 14-O-[((3-((S)-Phenylethyl)-(R*)-amino)-cyclopentan-1-(S*)-yl)-sulfanyl)-acetyl]-mutilin: 9.25, 9.35, 9.55 (3xb, 2H, (NH$_2$)$^+$), 7.4, 7.6 (2xm, 5H, arom.H), AB-system ($v_A$ = 3.22, $v_B$ = 3.32, H$_{22}$, J = 15 Hz), 3.05, 3.15 (2xb, 2H, SCH, NCH), 1.52 (d, 3H, C$_6$H$_5$CHCH$_3$N, J = 6.5 Hz), MS m/e: 582 (MH$^+$) |
| 26b | | | 14-O-[((3-((S)-Phenylethyl)-(S*)-amino)-cyclopentan-1-(S*)-yl)-sulfanyl)-acetyl]-mutilin: 9.25, 9.9.7 (2xb, 2H, (NH$_2$)$^+$), 7.4, 7.6 (2xm, 5H, arom.H), 3.22 (m, 2H, H$_{22}$), 4.3 (b, 1H, C$_6$H$_5$CHN), 1.52 (d, 3H, C$_6$H$_5$CHCH$_3$N, J = 6.5 Hz), MS m/e: 582 (MH$^+$) |
| 26c | | | 14-O-[((3-((R)-Phenylethyl)-(R*)-amino)-cyclopentan-1-(S*)-yl)-sulfanyl)-acetyl]-mutilin: 9.25, 9.35, 9.55 (3xb, 2H, (NH$_2$)$^+$), 7.4, 7.6 (2xm, 5H, arom.H), 3.22 (m, 2H, H$_{22}$), 4.3 (b, 1H, C$_6$H$_5$CHN), 3.05, 3.2 (2xb, 2H, SCH, NCH), 1.52 (d, 3H, C$_6$H$_5$CHCH$_3$N, J = 6.5 Hz), MS m/e: 582 (MH$^+$) |
| 26d | | | 14-O-[((3-((R)-Phenylethyl)-(S*)-amino)-cyclohexan-1-(S*)-yl)-sulfanyl)-acetyl]-mutilin: 9.3, 9.75 (2xb, 2H, (NH$_2$)$^+$), 7.4, 7.6 (2xm, 5H, arom.H), AB-system ($v_A$ = 3.18, $v_B$ = 3.30, H$_{22}$, J = 14.5 Hz), 4.3 (b, 1H, C$_6$H$_5$CHN), 1.58 (d, 3H, C$_6$H$_5$CHCH$_3$N, J = 6.5 Hz), MS m/e: 582 (MH$^+$). |
| 27a | 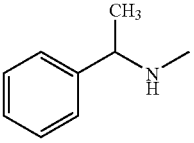 | C6 | 14-O-[(3-(R*)-((S)-Phenylethyl)amino)-cyclohexan-1-(R*)-yl)-sulfanyl)-acetyl]-mutilin: 8.95, 9.3 (2xb, 2H, (NH$_2$)$^+$), 7.4, 7.6 (2xm, 5H, arom. H), 3.15 (s, 2H, H$_{22}$), 4.5 (b, 1H, C$_6$H$_5$CHN), 3.35 (m, 1H, NCH), 2.9 (b, 1H, SCH), 1.55 (d, 3HC$_6$H$_5$CHCH$_3$N, J = 6.5 Hz) |
| 27b | | | 14-O-[(3-(S*)-((S)-Phenylethyl)amino)-cyclohexan-1-(R*)-yl)-sulfanyl)-acetyl]-mutilin: 8.8, 9.0 (2xb, 2H, (NH$_2$)$^+$), 7.4, 7.6 (2xm, 5H, arom.H), AB-system ($v_A$ = 3.35, $v_B$ = 3.4, 2H, H$_{22}$, J = 14 Hz), 4.45 (b, 1H, C$_6$H$_5$CHN), 3.18 (b, 2H, SCH, NCH), 1.55 (d, 3H, C$_6$H$_5$CHCH$_3$N, J = 6.5 Hz) |
| 27c | | | 14-O-[(3-(S*)-((R)-Phenylethyl)amino)-cyclohexan-1-(R*)-yl)-sulfanyl)-acetyl]-mutilin: 9.0, 9.5 (2xb, 2H, (NH$_2$)$^+$), 7.4, 7.6 (2xm, 5H, arom.H), 3.29 (s, 2H, H$_{22}$), 4.45 (b, 1H, C$_6$H$_5$CHN), 2.65 (b, 2H, SCH, NCH), 1.55 (d, 3H, C$_6$H$_5$CHCH$_3$N, J = 6.5 Hz) |
| 27d | | | 14-O-[(3-(R*)-((R)-Phenylethyl)amino)-cyclohexan-1-(R*)-yl)-sulfanyl)-acetyl]-mutilin: 8.95, 9.45 (2xb, 2H, (NH$_2$)$^+$), 7.4, 7.6 (2xm, 5H, arom. H), 3.29 (s, 2H, H$_{22}$), 4.55 (b, 1H, C$_6$H$_5$CHN), 2.9 (b, 1H, SCH), 1.55 (d, 3H, C$_6$H$_5$CHCH$_3$N, J = 6.5 Hz) |
| 27e | | | 14-O-[(3-(R*)-((R)-Phenylethyl)amino)-cyclohexan-1-(S*)-yl)-sulfanyl)-acetyl]-mutilin: 9.15, 9.45 (2xb, 2H, (NH$_2$)$^+$), 7.4, 7.6 (2xm, 5H, arom.H), AB-system ($v_A$ = 3.38, $v_B$ = 3.42, H$_{22}$, J = 14 Hz), 4.55 (b, 1H, C$_6$H$_5$CHN), 2.6 (b, 2H, NCH, SCH), 1.55 (d, 3HC$_6$H$_5$CHCH$_3$N, J = 6.5 Hz) |
| 27f | | | 14-O-[(3-(S*)-((R)-Phenylethyl)amino)-cyclohexan-1-(S*)-yl)-sulfanyl)-acetyl]-mutilin: 9.0, 9.35 (2xb, 2H, (NH$_2$)$^+$), 7.4, 7.6 (2xm, 5H, arom.H), AB-system ($v_A$ = 3.12, $v_B$ = 3.25, H$_{22}$, J = 15 Hz), 4.5 (b, 1H, C$_6$H$_5$CHN), 2.9 (b, 1H, SCH), 1.55 (d, 3HC$_6$H$_5$CHCH$_3$N, J = 6.5 Hz) |

TABLE 1-continued

| EX | R_{EX} | CYC | DATA |
|---|---|---|---|
| 28 | (1H-benzimidazol-2-ylmethyl)methylamine structure | C5 | 14-O-{[3(R/S)-(1H-Benzoimidazol-2-ylmethylamino)-cyclopent-1(R/S)-ylsulfanyl]-acetyl}-mutilin: 9.9 (b, 2H, (NH$_2$)$^+$), 7.65, 7.3 (2xm, 4H, arom.H), 3.7, 3.85 (2xm, 1H, NCH), 3.45 (d, 2H, NCH$_2$, J = 5.9 Hz), 3.3 (m, 2H, H$_{22}$), 3.45, 3.15 (2xm, 1H, SCH), MS m/e: 608 (MH$^+$) |
| 29a | N,N-dimethyl(methyl)amine | C5 | 14-O-{[(3(S*)-Dimethylamino-cyclopent-1(R*)-yl)-sulfanyl]-acetyl}-mutilin + 1(S*)3(R*) Diastereomer: 10.02 (b, 1H, NH$^+$), 3.48 (m, 1H, NCH)), 3.2 (m, 1H, SCH), 2.7 (s, 6H, N(CH$_3$)$_2$), MS m/e: 506 (M$^+$) |
| 29b | | | 14-O-{[(3(S*)-Dimethylamino-cyclopent-1(S*)-yl)-sulfanyl]-acetyl}-mutilin + 1(R*)3(R*) Diastereomer: 10.2 (b, 1H, NH$^+$), 3.65 (m, 1H, NCH)), 3.25 (m, 1H, SCH), 2.7 (s, 6H, N(CH$_3$)$_2$), MS m/e: 506 (M$^+$) |
| 30a | N,N-diethyl(methyl)amine | C5 | 14-O-{[(3(S*)-Diethylamino-cyclopent-1(R*)-yl)-sulfanyl]-acetyl}-mutilin + 1(S*) 3(R*) Diastereomer): 10.0 (b, 1H, NH$^+$), 3.6 (b, 1H, NCH)), 3.02-3.15 (2xb, 4H, NCH$_2$CH$_3$), 1.15 (bt, 3H, CH$_3$CH$_2$). MS m/e: 534 (M$^+$) |
| 30b | | | 14-O-{[(3(S*)-Diethylamino-cyclopent-1(S*)-yl)-sulfanyl]-acetyl}-mutilin + 1(R*) 3(R*)-Diastereomer: 10.3 (b, 1H, NH$^+$), 3.71 (m, 1H, NCH)), AB-system (v$_A$ = 3.28, v$_B$ = 3.35, H$_{22}$, J = 14.5 Hz), 3.05-3.15 (2xb, 4H, NCH$_2$CH$_3$), 1.15 (t, 3H, CH$_3$CH$_2$, J = 4.4 Hz). MS m/e: 534 (M$^+$) |
| 31 | N,N-diethyl(methyl)amine | C7 | 14-O-[(3-(R/S)-Diethylamino-cycloheptane-1(R/S)-yl)-sulfanylacetyl]-mutilin: 10.05 (b, 1H, N(C$_2$H$_5$)$_2$H$^+$), 3.3-3.5 (m, 3H, H$_{11}$, H$_{22}$), 3.05, 3.12, 3.2 (3xb, 5H, NCH$_2$CH$_3$, NCH), 1.95 (b, 1H, SCH), 1.24, 1.28 (2xt, 6H, NCH$_2$CH$_3$, J = 8.2 Hz) |
| 32 | N-cyclopropyl(methyl)amine | C5 | 14-O-{[(3-(R/S)-Cyclopropylamino-cyclopent-1(R/S)-yl)-sulfanyl]-acetyl}-mutilin: 9.1 (b, 2H, (NH$_2$)$^+$), 3.15, 3.55, 3.65 (3xm, 2H, 2xNCH), 3.3 (m, 2H, H$_{22}$), 2.65 (b, 1H, SCH), 0.7, 0.9 (2xm, 4H, Cyclopropyl-H). |
| 33a | N-cyclopropyl(methyl)amine | C6 | 14-O-{[(3-(S)-Cyclopropylamino-cyclohexan-1(R)-yl)-sulfanyl]-acetyl}-mutilin + 1S3R-Diastereomer: 9.0 (b, 2H, (NH$_2$)$^+$), 3.33 (m, 2H, H$_{22}$), 2.68, 2.75, 3.08 (3xm, 3H, 2xNCH, SCH), 0.73, 0.85 (2xm, 4H, Cyclopropyl-H), MS m/e: 532 (MH$^+$). |
| 33b | | | 14-O-{[(3-(R)-Cyclopropylamino-cyclohexan-1(R)-yl)-sulfanyl]-acetyl}-mutilin + 1S3S-Diastereomer: 8.9 (b, 2H, (NH$_2$)$^+$), 3.2-3.35 (m, 4H, H$_{22}$, NCH, SCH), 2.65 (m, 1H, NCH), 0.74, 0.83 (2xm, 4H, Cyclopropyl-H), MS m/e: 532 (MH$^+$). |
| 34a | 4-methylmorpholine | C6 | 14-O-[((3-(R*)-(Morpholin-4-yl)-cyclohexan-1-(S*)-yl)-sulfanyl)-acetyl]-mutilin: 10.5 (b, 1H, NH$^+$), 3.3-3.45 (m, 4H, H$_{22}$, NCH, SCH), 3.75, 3.95 (2xb, 4H, OCH$_2$), 3.05, 3.25 (2xb, 4H, NCH$_2$) |
| 34b | | | 14-O-[((3-(R*)-(Morpholin-4-yl)-cyclohexan-1-(R*)-yl)-sulfanyl)-acetyl]-mutilin: 10.5 (b, 1H, NH$^+$), AB-system (v$_A$ = 3.35, v$_B$ = 3.4, 2H, H$_{22}$, J = 14 Hz) 3.75, 3.95 (2xb, 4H, OCH$_2$), 3.15, 3.25 (2xb, 4H, NCH$_2$), 3.05 (b, 1H, NCH) |
| 35 | N-methyl(1H-imidazol-2-yl)amine | C5 | 14-O-{[3(R/S)-(1H-Imidazol-2-ylamino)-cyclopent-1(R/S)-ylsulfanyl]-acetyl}-mutilin: 12.0 (s, 2H, imidazole-NH), 8.1 (m, 2H, (NH$_2$)$^+$), 6.9 (s, 2H, imidazole-H), 3.85, 4.0 (2xm, 1H, NCH), 3.3 (m, 2H, H$_{22}$), 3.1 (m, 1H, SCH), MS m/e: 544 (MH$^+$) |

TABLE 1-continued

| EX | R_{EX} | CYC | DATA |
|---|---|---|---|
| 36 | 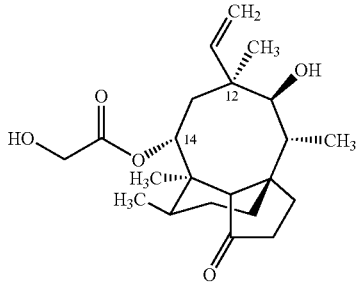 | C5 | 14-O-{[3(R/S)-(1H-Benzoimidazol-2-ylamino)-cyclopent-1(R/S)-ylsulfanyl]-acetyl}-mutilin: 12.6 (b, 2H, (NH$_2$)$^+$), 9.1 (d, 1H, NH, J = 7.5 Hz), 7.4, 7.2 (2xm, 4H, arom.H), 4.1 (m, 1H, NCH), 3.3 (m, 2H, H$_{22}$), 2.6 (m, 1H, SCH), MS m/e: 594 (MH$^+$) |

In TABLE 1
in column "EX" the Example number is indicated.
in all compounds listed the subsituent "R$_{EX}$" is in the 3-position of the corresponding cycloalkyl,
"CYC" means cycloalkylene and in column "CYC" there is indicated the ring member number of the corresponding cycloalkylene and optionally cycloalkyl substitution (C5, C6 or C7, respectively, means, beside R$_{EX}$-substitution, unsubstituted cyclopentylene, cyclohexylene or cyloheptylene, respectively),
all compounds are obtained in free form and in the form of a hydrochloride salt,
in column "DATA" H$^1$-NMR data is indicated (determined in d$_6$-DMSO at 400 or 500 MHz) and optionally mass spectroscopy data (MS-ESI); and all data indicated is data obtained from the hydrochloride salt of the corresponding compound of formula EX, except for Example 11 and 12 where data is obtained from the free form,
the $^1$H-NMR-data of the tricylic mutilin are indicated in Example 1a. In the other Examples only data of the C-14 side chain is indicated, unless there is substantial change concerning data of the mutilin ring.

The invention claimed is:

1. A compound having formula Ip:

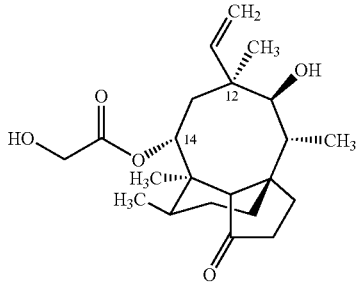

wherein,

R is hydrogen or (C$_{1-8}$)alkyl,

R$_1$ is (C$_{3-12}$)cycloalkyl, unsubstituted (C$_{1-8}$)alkyl, or (C$_{1-8}$)alkyl substituted by
  hydroxy,
  halogen,
  (C$_{1-6}$)alkyloxycarbonyl;
  (C$_{1-4}$)alkylaminocarbonyl;
  (C$_{3-8}$)cycloalkyl or cyclohexyl,
  (C$_{6-18}$)aryl, or
  a heterocyclic group comprising 3 to 7 ring members, 1 to 4 heteroatoms selected from the group consisting of N, O and S, optionally anellated with another ring system, R$_2$ is hydrogen or (C$_{1-4}$)alkyl, q is a number selected from 0, 1 and 2; and the group (NRR$_1$) is in position 3 or in position 4 of the cycloalkyl ring.

2. The compound according to claim 1 having formula Ipp:

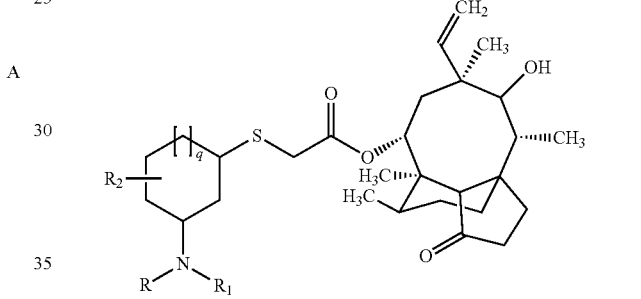

wherein R, R$_1$ and q are as defined in claim 1.

3. A compound as claimed in claim 1 in the form of a salt.

4. A pharmaceutical composition comprising a compound according to claim 1, optionally in the form of a salt, in association with at least one pharmaceutical excipient, optionally further comprising another pharmaceutically active agent.

5. The compound as claimed in claim 2 in the form of a salt.

6. A pharmaceutical composition comprising a compound according to claim 2, optionally in the form of a salt, in association with at least one pharmaceutical excipient, optionally further comprising another pharmaceutically active agent.

7. A compound according to claim 1, which is selected from the group consisting of:

14-O—[(3-Diethylamino-cyclohexan-1-yl)-sulfanylacetyl]-mutilin,
14-O-{[(3-Methylamino-cyclopent-1-yl)-sulfanyl]-acetyl}-mutilin,
14-O-{[(3-Ethylamino-cyclopent-1-yl)-sulfanyl]-acetyl}-mutilin,
14-O-{[(3-Ethylamino-1-methyl-cyclopent-1-yl)-sulfanyl]-acetyl}-mutilin,
14-O-{[(3-Ethylamino-2-methyl-cyclopent-1-yl)-sulfanyl]-acetyl}-mutilin,
14-O-{[3-Ethylamino-cyclohexanylsulfanyl]-acetyl}-mutilin,
14-O-{[3-(sec-Butylamino)-cyclopent-1-ylsulfanyl]-acetyl}-mutilin, 14-O-[((3-(sec-Butylamino)-cyclohexan-1-yl)-sulfanyl)-acetyl]-mutilin,
14-O—[((1-(sec-Butylamino)-cycloheptan-3-yl)-sulfanyl)-acetyl]-mutilin,
14-O-{[3-(2,2,2-Trifluoro-ethylamino)-cyclopent-1-yl-sulfanyl]-acetyl}-mutilin,
14-O-{[3-(2,2,2-Trifluoro-ethylamino)-cyclohexan-1-yl-sulfanyl]-acetyl}-mutilin,
14-O-{[3-(2,2-Difluoro-ethylamino)-cyclohexan-1-ylsulfanyl]-acetyl}-mutilin,
14-O-{[(3-(2-Hydroxy-ethylamino)-cyclopent-1-yl)-sulfanyl]-acetyl}-mutilin,
14-O-{[3-(2-Hydroxy-propylamino)-cyclopent-1-ylsulfanyl]-acetyl}-mutilin,
14-O-[((3-(1-Isopropyl-2-hydroxy-ethylamino)-cyclopent-1-yl)-sulfanyl)-acetyl]-mutilin,
14-O-[((3-(1-Isopropyl-2-hydroxy-ethylamino)-cyclohexan-1-yl)-sulfanyl)-acetyl]-mutilin,
14-O-{[3-(2-Hydroxy-1-hydroxymethyl-1-methyl-ethylamino)-cyclopent-1-ylsulfanyl]-acetyl}-mutilin,
14-O-{[3-(2-Hydroxy-1,1-bis-hydroxymethyl-ethylamino)-cyclopent-1-ylsulfanyl]-acetyl}-mutilin,
14-O-[((3-(Methoxycarbonyl-methylamino)-cyclopent-1-yl)-sulfanyl)-acetyl]-mutilin,
14-O—[((3-(Ethoxycarbonyl-methylamino)-cyclopent-1-yl)-sulfanyl)-acetyl]-mutilin,
14-O—[(((3-(Isopropoxycarbonyl-methylamino)-cyclopent-1-yl)-sulfanyl)-acetyl]-mutilin,
14-O-{[3-(Methoxypropionyl-2-amino)-cyclopent-1-yl-sulfanyl]-acetyl}-mutilin,
14-O-{[3-(Isopropoxypropionyl-2-amino)-cyclopent-1-yl-sulfanyl]-acetyl}-mutilin,
14-O-{[(3-Methylcarbamoylmethylamino-cyclopent-1-yl)-sulfanyl]-acetyl}-mutilin,
14-O—[(((3-(1-Cyclohexylethyl)-amino)-cyclohexan-1-yl)-sulfanyl)-acetyl]-mutilin,
14-O—[(((3-(Phenylethyl)-amino)-cyclopentan-1-yl)-sulfanyl)-acetyl]-mutilin,
14-O—[(((3-(Phenylethyl)-amino)-cyclohexan-1-yl)-sulfanyl)-acetyl]-mutilin,
14-O-{[3-(1H-Benzoimidazol-2-ylmethylamino)-cyclopent-1-ylsulfanyl]-acetyl}-mutilin,
14-O-{[(3-Dimethylamino-cyclopent-1-yl)-sulfanyl]-acetyl}-mutilin,
14-O-{[(3-Diethylamino-cyclopent-1)-yl)-sulfanyl]-acetyl}-mutilin,
14-O-[((3-Diethylamino-cycloheptan-1-yl)-sulfanyl)-acetyl]-mutilin,
14-O-{[(3-Cyclopropylamino-cyclopent-1-yl)-sulfanyl]-acetyl}-mutilin,
14-O-{[(3-Cyclopropylamino-cyclohexan-1-yl)-sulfanyl]-acetyl}-mutilin,
14-O-[((3-(Morpholin-4-yl)-cyclohexan-1-yl)-sulfanyl)-acetyl]-mutilin,
14-O-{[(3-(1H-Imidazol-2-ylamino)-cyclopent-1-yl)-sulfanyl]-acetyl}-mutilin, and
14-O-{[(3-(1H-Benzoimidazol-2-ylamino)-cyclopent-1-yl)-sulfanyl]-acetyl}-mutilin.

8. A compound as claimed in claim 7 in the form of a salt.

9. A pharmaceutical composition comprising a compound according to claim 7, optionally in the form of a salt, in association with at least one pharmaceutical excipient, optionally further comprising another pharmaceutically active agent.

10. A compound having formula Ip:

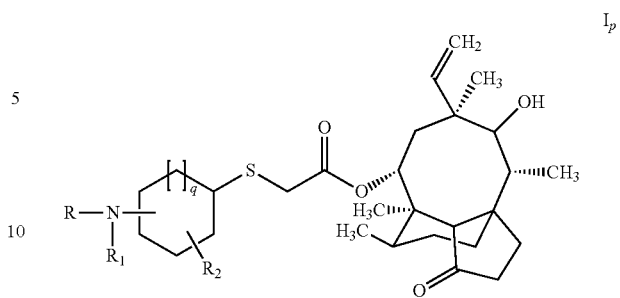

wherein
R is hydrogen or $(C_{1-8})$alkyl,
$R_1$ is unsubstituted $(C_{1-8})$alkyl,
$R_2$ is hydrogen or $(C_{1-4})$alkyl,
q is 1; and
the group $(NRR_1)$ is in position 3 or in position 4 of the cycloalkyl ring.

11. The compound according to claim 10 having formula Ipp:

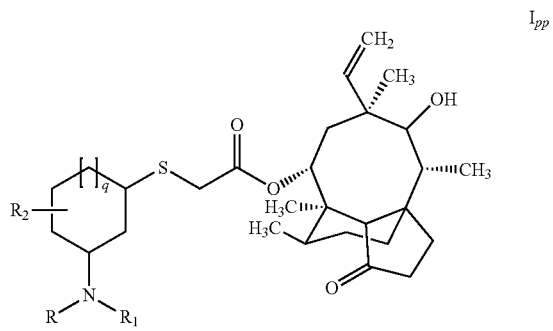

wherein R, $R_1$ and q are as defined in claim 1.

12. A compound according claim 10, which is selected from the group consisting of
14-O-[(3-Diethylamino-cyclohexan-1-yl)-sulfanylacetyl]-mutilin,
14-O-{[3-Ethylamino-cyclohexanylsulfanyl]-acetyl}-mutilin,
14-O-[((3-(sec-Butylamino)-cyclohexan-1-yl)-sulfanyl)-acetyl]-mutilin,
14-O-{[3-(2,2,2-Trifluoro-ethylamino)-cyclohexan-1-yl-sulfanyl]-acetyl}-mutilin,
14-O-{[3-(2,2-Difluoro-ethylamino)-cyclohexan-1-ylsulfanyl]-acetyl}-mutilin,
14-O-[((3-(1-Isopropyl-2-hydroxy-ethylamino)-cyclohexan-1-yl)-sulfanyl)-acetyl]-mutilin,
14-O—[(((3-(1-Cyclohexylethyl)-amino)-cyclohexan-1-yl)-sulfanyl)-acetyl]-mutilin,
14-O—[(((3-(Phenylethyl)-amino)-cyclohexan-1-yl)-sulfanyl)-acetyl]-mutilin,
14-O-{[(3-Cyclopropylamino-cyclohexan-1-yl)-sulfanyl]-acetyl}-mutilin, and
14-O-[((3-(Morpholin-4-yl)-cyclohexan-1-yl)-sulfanyl)-acetyl]-mutilin.

13. A compound of claim 10 in the form of a salt.

14. A pharmaceutical composition comprising a compound of claim 10, optionally in the form of a salt, in association with at least one pharmaceutical excipient.

15. The compound according to claim 11 in the form of a salt.

16. A pharmaceutical composition comprising a compound of claim 11, optionally in the form of a salt, in association with at least one pharmaceutical excipient.

17. A compound according to claim 12 in the form of a salt.

18. A pharmaceutical composition comprising a compound of claim 12, optionally in the form of a salt, in association with at least one pharmaceutical excipient.

* * * * *

UNITED STATES PATENT AND TRADEMARK OFFICE
CERTIFICATE OF CORRECTION

PATENT NO. : 8,343,972 B2
APPLICATION NO. : 11/997637
DATED : January 1, 2013
INVENTOR(S) : Mang et al.

Page 1 of 1

It is certified that error appears in the above-identified patent and that said Letters Patent is hereby corrected as shown below:

Column 25
Line 27-40, change

"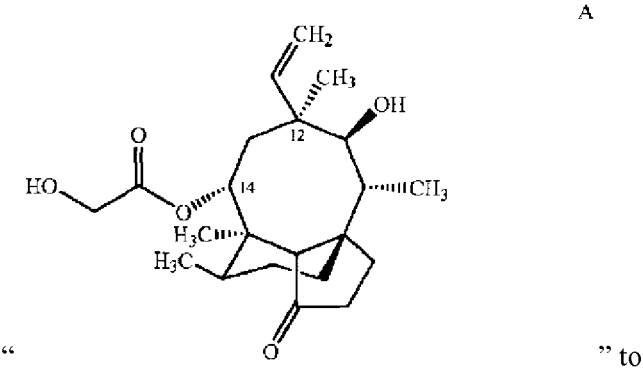" to

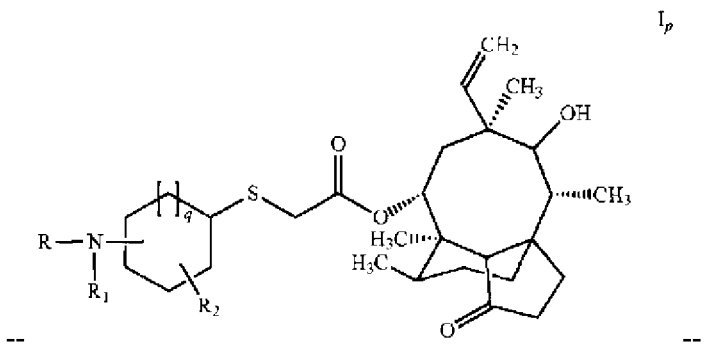

--

Signed and Sealed this
Nineteenth Day of March, 2013

Teresa Stanek Rea
*Acting Director of the United States Patent and Trademark Office*